United States Patent [19]

Sutter et al.

[11] Patent Number: 5,374,639
[45] Date of Patent: Dec. 20, 1994

[54] BENZOTRIAZOLESULFONIC ACID DERIVATIVES AS MICROBICIDES

[75] Inventors: Marius Sutter, Binningen; Urs Müller, Münchenstein; Bernhard Hostettler, Zürich; Peter Ackermann, Pfeffingen; Yasuchika Yamaguchi, Basel, all of Switzerland

[73] Assignee: Ciba-Geigy Corporation, Ardsley, N.Y.

[21] Appl. No.: 991,677

[22] Filed: Dec. 16, 1992

[30] Foreign Application Priority Data

Dec. 20, 1991 [CH]  Switzerland ............... 3812/92-2

[51] Int. Cl.⁵ ............................................. C07D 249/18
[52] U.S. Cl. ............................ 514/338; 514/253; 514/269; 544/238; 544/298; 544/405; 546/271
[58] Field of Search .................. 548/259; 546/271; 514/338

[56] References Cited

U.S. PATENT DOCUMENTS

| | | | |
|---|---|---|---|
| 2,943,017 | 6/1960 | Sasse et al. | 548/259 |
| 3,966,251 | 6/1976 | Bohner | 548/259 |
| 4,076,828 | 2/1978 | Haugwitz et al. | 546/271 |
| 4,242,507 | 12/1980 | Itoh | 548/259 |
| 4,734,427 | 3/1988 | Riebel et al. | 514/398 |
| 4,943,574 | 7/1990 | Raemaekers et al. | 546/271 |
| 4,970,219 | 11/1990 | Effland et al. | 514/339 |
| 5,190,574 | 3/1993 | Pearson | 548/259 |
| 5,322,853 | 6/1994 | Ackerman | 514/359 |

FOREIGN PATENT DOCUMENTS

| | | |
|---|---|---|
| 566599 | 4/1958 | Belgium . |
| 0238824 | 9/1987 | European Pat. Off. . |
| 0299446 | 1/1989 | European Pat. Off. . |
| 0355049 | 2/1990 | European Pat. Off. ............ 546/271 |
| 0367242 | 5/1990 | European Pat. Off. . |
| 462931 | 12/1991 | European Pat. Off. . |
| 1046937 | 8/1959 | Germany . |
| 3406011 | 8/1986 | Germany . |
| 0885843 | 12/1961 | United Kingdom . |
| 2157679 | 10/1985 | United Kingdom . |

OTHER PUBLICATIONS

Chem. Reviews 46, 1 (1950), Frederick Benson et al.
Chemical Abstracts, 104, 50880 y (1986).

*Primary Examiner*—Donald G. Daus
*Attorney, Agent, or Firm*—Edward McC. Roberts; George R. Dohmann

[57] ABSTRACT

Benzotriazolesulfonic acid derivatives of formula I

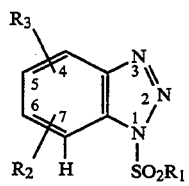

(I)

wherein $R_3=R_4X$ and $R_4$ is an unsaturated 6-membered heterocycle having a maximum of 2 nitrogen atoms, it being possible for the heterocycle to be substituted, and X is oxygen or sulfur, while $R_1$ and $R_2$ are as defined herein, are valuable microbicides. They can be used in plant protection in the form of suitable compositions, for example for controlling fungal diseases.

16 Claims, No Drawings

BENZOTRIAZOLESULFONIC ACID DERIVATIVES AS MICROBICIDES

The present invention relates to novel benzotriazolesulfonic acid derivatives of the following formula I. It relates furthermore to the preparation of those compounds and to agrochemical compositions that comprise at least one of those compounds as active ingredient. The invention also relates to the preparation of the said compositions and to the use of the compounds or compositions for controlling or preventing an attack on plants by phytopathogenic microorganisms, especially fungi.

The compounds according to the invention correspond to the general formula I

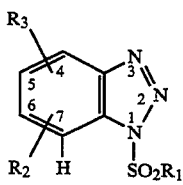
(I)

wherein the $R_1SO_2$ group occupies the 1- or the 3-position and, in relation to the substituents $R_3$ and $R_2$, forms pure isomers or a mixture of structural isomers, and wherein the substituents are defined as follows:

$R_3 = R_4X$ $X$ = oxygen or sulfur;

$R_4$ = an unsaturated 6-membered heterocycle that has a maximum of two nitrogen atoms and that may be unsubstituted or substituted by at least one of the substituents halogen, $C_1$-$C_6$alkyl, $C_1$-$C_6$alkoxy, $C_1$-$C_6$alkylthio, $C_1$-$C_6$haloalkyl, $C_1$-$C_6$haloalkoxy, $C_3$-$C_6$cycloalkyl, cyano, nitro, —COO($C_1$-$C_6$alkyl) and $N(R')(R'')$;

$R_2$ = hydrogen, halogen, $C_1$-$C_4$alkyl, $C_1$-$C_4$alkoxy, $C_1$-$C_4$haloalkyl, $C_1$-$C_4$haloalkoxy or —N(alk)$_2$;

$R_1$ = $C_1$-$C_4$alkyl, $C_3$-$C_4$haloalkyl, $C_3$-$C_6$cycloalkyl, or —N(alk)$_2$, wherein each alk is $C_1$-$C_4$alkyl and, whether the same or different, is bonded to N;

$R'$ and $R''$ = independently, hydrogen or $C_1$-$C_4$alkyl.

Depending on the number of carbon atoms indicated, alkyl on its own or as a component of another substituent, such as haloalkyl, alkoxy or haloalkoxy, is to be understood as being, for example, the following straight-chain or branched groups: methyl, ethyl, propyl, butyl, pentyl, hexyl and their isomers, isopropyl, isobutyl, sec-butyl, sec-amyl, tert-amyl and tert-butyl. Halogen and halo are fluorine, chlorine, bromine or iodine. Haloalkoxy is therefore a mono- to perhalogenated alkoxy radical, for example $OCH_2F$, $OCHF_2$, $OCHFCH_3$, $OCH_2CH_2Br$, $OCF_2CHFCl$ etc.

The term cycloalkyl denotes cyclopropyl, cyclobutyl, cyclopentyl or cyclohexyl.

The unsaturated 6-membered heterocycles referred to are to be understood as being pyridine, pyrimidine, pyrazine and pyridazine.

The compounds of formula I are oils or solids that are stable at room temperature and are distinguished by valuable microbicidal properties. They can be used preventively and curatively in the agricultural sector or related fields for controlling plant-destructive microorganisms. When used at low concentrations, the compounds of formula I according to the invention are distinguished not only by excellent microbicidal, especially fungicidal, activity, but also by especially good plant tolerability.

Within the scope of formula I, importance is attached to those compounds wherein $R_4$ is a substituted pyridine, pyrimidine, pyrazine or pyridazine ring [subgroup Ib] and, of those, compounds wherein the 6-membered heterocycle is substituted by from one to three substituents selected from halogen, methyl, ethyl, isopropyl, methoxy, $C_1$-$C_2$haloalkyl wherein the halogen is F and/or Cl, $CF_3O$, $CHF_2O$, cyclopropyl and nitro [subgroup IC]. Of the important groups of compounds within the scope of formula I mention should be made of those wherein the 6-membered heterocycle is substituted by from one so three substituents selected from halogen, methyl, ethyl, isopropyl, methoxy, $CFC_2$haloalkyl wherein the halogen is F and/or Cl, $CF_3O$, $CHF_2O$ and nitro [subgroup IC].

One of the especially important groups of compounds within the scope of formula I is that wherein the 6-membered heterocycle is unsubstituted or mono- to tri-substituted pyridine and $R_2$ is hydrogen, fluorine, chlorine, bromine, methyl, methoxy, $CF_3$, $CF_3O$ or $CHF_2O$ [subgroup Id], especially those wherein $R_2$ is hydrogen, chlorine or bromine [subgroup Ie].

One of the preferred groups of compounds within the scope of subgroup Id is that wherein the pyridine ring is substituted by a maximum of three substituents selected from halogen, $C_1$-$C_4$alkyl, $C_1$-$C_4$alkoxy, $C_1$-$C_4$haloalkyl, $C_1$-$C_4$haloalkoxy and cyclopropyl [subgroup IF], and within that group especially those compounds wherein the pyridine ring is substituted by a maximum of three substituents selected from halogen, $C_1$-$C_4$alkyl, $C_1$-$C_4$alkoxy, $C_1$-$C_4$haloalkyl and $C_1$-$C_4$haloalkoxy [subgroup If], especially those wherein the pyridine ring is substituted at least by $CF_3$ [subgroup Ig].

Another preferred group of compounds within the scope of formula I is that wherein the 6-membered heterocycle is unsubstituted or mono- to tri-substituted pyrimidine and $R_2$ is hydrogen, fluorine, chlorine, bromine, methyl, methoxy, $CF_3$, $CF_3O$ or $CHF_2O$ [subgroup Ih], especially those wherein $R_2$ is hydrogen, chlorine or bromine [subgroup Ii].

Within subgroup Ih an important subgroup is formed by compounds wherein the pyrimidine ring is substituted by a maximum of three substituents selected from halogen, $C_1$-$C_4$alkyl, $C_1$-$C_4$alkoxy, $C_1$-$C_4$haloalkyl and $C_1$-$C_4$haloalkoxy [subgroup Ij].

A preferred structural type within the scope of formula I and the subgroups thereof referred to herein comprises those compounds wherein $R_1$ is methyl. Another important structural type of formula I and the subgroups thereof comprises benzotriazole derivatives wherein the 4-position is unsubstituted.

The compounds of formula I can be prepared

1 ) by reacting a compound of formula II

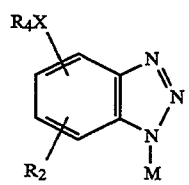
(II)

with a compound of formula III

 (III), wherein X, $R_1$, $R_2$ and $R_4$ are as defined for formula I and M is hydrogen or an alkali metal, preferably sodium, potassium or lithium, and Q is a halogen atom, preferably chlorine, or the radical O—$SO_2$—$R_1$, in an inert solvent, in the presence or absence of a base, at temperatures of from −30° to 180° C., preferably from −10° to 80° C., under normal pressure, reduced or elevated pressure, preferably under normal pressure.

If the substituents are in position 5 and/or 6, two isomers are formed with the sulfonyl group in the 1-position and/or the 3-position. The invention relates also to those isomers, as well as to any desired mixtures thereof. Only one of those structures is shown below in each case, but mixtures are always intended.

Compounds of formula I can also be prepared
2) by diazotising a compound of formula IV

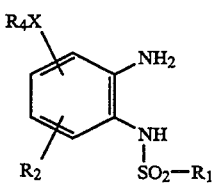
(IV)

wherein X, $R_1$, $R_2$ and $R_4$ are as defined for formula I, either a) with an inorganic nitrite in a solvent, preferably in water or in a mixture of water with an alcohol, preferably methanol or ethanol, or in a mixture of water with an ether, preferably dioxane or dimethoxyethane, in the presence of an acid, preferably acetic acid, at temperatures of from −30° to 180° C., preferably from 0° to 80° C.; or b) with an organic nitrite, preferably ethyl nitrite, amyl nitrite or tert-butyl nitrite, in a solvent, preferably an alcohol, such as methanol or ethanol, or an ether, such as dioxane or dimethoxyethane, in the presence or absence of an acid, at temperatures of from −30° to 180° C., preferably from 0° to 80° C., under normal pressure or elevated pressure.

The compounds of formula II wherein M=H are prepared
3) by diazotising a compound of formula V

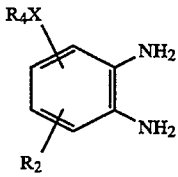
(V)

wherein $R_4X$ and $R_2$ are as defined for formula IIa, either 3a) with an inorganic nitrite in a solvent, preferably in water or in a mixture of water with an alcohol, preferably methanol or ethanol, or in a mixture of water with an ether, preferably dioxane or dimethoxyethane, in the presence of an acid, preferably acetic acid, at temperatures of from −30° to 180° C., preferably from 0° to 80° C.; or 3b) with an organic nitrite, preferably ethyl nitrite, amyl nitrite or tert-butyl nitrite, in a solvent, preferably an alcohol, such as methanol or ethanol, or an ether, such as dioxane or dimethoxyethane, in the presence or absence of an acid, at temperatures of from −30° to 180° C., preferably from 0° to 80° C., under normal pressure or elevated pressure: or 4) by reacting a compound of formula VI

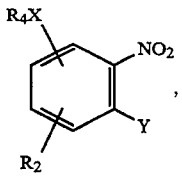
(VI)

wherein $R_4X$ and $R_2$ are as defined for formula IIa and Y is a halogen atom, preferably fluorine or chlorine, with hydrazine or hydrazine hydrate in a solvent, preferably an alcohol, such as methanol or ethanol, in the presence of an acidbinding agent, preferably sodium carbonate, potassium carbonate or triethylamine, at the reflux temperature of the reaction medium, to form a compound of formula VII

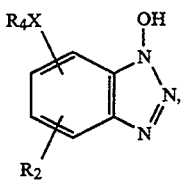
(VII)

which is then reacted with a chloroketone

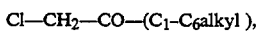
Cl—$CH_2$—CO—($C_1$-$C_6$alkyl), preferably chloroacetone, in an inert solvent in the presence of a base, at temperatures of from 40° to 140° C., preferably from 60° to 120° C.

The following inert solvents are suitable for the processes described above: aliphatic, cycloaliphatic or aromatic hydrocarbons, for example hexane, cyclohexane, toluene, xylene, petroleum ether or ligroin; chlorinated hydrocarbons, for example methylene chloride, chloroform, carbon tetrachloride, chlorobenzene; ethers, for example diethyl ether, diisopropyl ether, furan, tetrahydrofuran, dioxane; ketones, for example acetone. methyl ethyl ketone; alcohols, for example methanol, ethanol, isopropanol; esters, for example ethyl acetate, butyl acetate; nitriles, for example acetonitrile, propionitrile; acid amides, for example dimethylformamide; sulfones and sulfoxide, for example dimethyl sulfoxide and sulfolane.

Suitable bases or acid-binding agents are, for example, hydroxides, carbonates, hydrogen carbonates or alcoholales of alkali metals and alkaline earth metals; and also tertiary amines, for example triethylamine, triisopropylamine, pyridine or 4-N,N-dimethylaminopyridine.

The processes described above correspond to methods of synthesis that are known from the literature. They are described, for example, in Chem. Reviews 46, 1 (1950) and in German Offenlegungsschrift 34 06 011. The synthesis of starting compounds of the type of formula IV is known analogously from U.S. Pat. No. 2,943,017.

Compounds with benzotriazolesulfonic acid structures are already known. Such compounds are described in Patent Specifications DE-1 046 937, GB-885 843 and U.S. Pat. No. 2,943,017 as active ingredients that can be used as fungicides. Compounds of formula V can be prepared by reducing the nitro-group-containing compounds of formula VIII. There may be used as reducing agents the conventional reducing agents such as iron (Bechamps reduction), tin(II) chloride, or hydrogen with a catalyst, such as Raney nickel or palladium/charcoal. The reaction conditions correspond to those given in the literature (for example Houben Weyl "Methoden der organischen Chemie").

Compounds of formula VIII can be obtained from compounds of formula IX by reaction with correspondingly substituted 2-halopyridines, 2-halopyrazines, 3-halopyridines, 2-halopyrimidines or 4-halopyrimidines (formula group X). The reaction is carried out in an inert organic solvent, preferably in a polar solvent, such as DMF, DMSO or DMA, or a ketone, such as acetone or ethyl methyl ketone, an alcohol, such as ethanol, propanol or butanol, or an ether, such as diethyl ether or tetrahydrofuran, in the presence of a base, preferably an alkali metal (hydrogen) carbonate or hydroxide, such as $Na_2CO_3$, $K_2CO_3$, NaOH or KOH, or an amine, such as triethylamine or pyridine. The reaction temperature is from 0° C. to +150° C., preferably 80°–120° C.

An alternative method of obtaining compounds of formula VIII is the reaction of a compound of formula XI with a correspondingly substituted pyridine, pyrimidine, pyridazine or pyrazine carrying a hydroxy group or a mercapto group (formula group XII). The reaction takes place preferably under the same conditions as those described above.

The compounds of formulae IX, X, XI and XII are either known in the literature or can be prepared by known methods.

In the case where X=S, it is also possible to use compounds of formula IX masked as thiocyanate (U.S. Pat. No. 4,076,828).

(for definition of X see below reaction Scheme 1)

Compounds of formula II wherein M=hydrogen can also be synthesised from compounds of formula XIII by reaction with 2-halopyridines, 2-halopyrazines, 3-halopyridazines or 2- or 4-halopyrimidines (formula group X). The reaction is carried out in an inert organic solvent, preferably in a polar solvent, such as DMF, DMSO or DMA, or a ketone, such as acetone or ethyl methyl ketone, an alcohol, such as ethanol, propanol or butanol, or an ether, such as diethyl ether or tetrahydrofuran, in the presence of a base. Examples of preferred bases are carbonates, such as sodium carbonate or potassium carbonate, but also hydroxides, such as potassium hydroxide or sodium hydroxide, or amines, such as triethylamine or pyridine. The reaction temperature is from 0° C. to 150° C., preferably from 80° C. to 120° C.

Compounds of formula XIII can be prepared from compounds of formula XIV by diazotisation, either a) with an inorganic nitrite in a solvent, preferably in water or in a mixture of water with an alcohol, preferably methanol or ethanol, or in a mixture of water with an ether, preferably dioxane or dimethoxyethane, in the presence of an acid, preferably acetic acid, at temperatures of from −30° to 180° C., preferably from 0° to 80° C.; or b) with an organic nitrite, preferably ethyl nitrite, amyl nitrite or tert-butyl nitrite, in a solvent, preferably an alcohol, such as methanol or ethanol, or an ether, such as dioxane or dimethoxyethane, in the presence or absence of an acid, at temperatures of from −30° to 180° C., preferably from 0° to 80° C., under normal pressure or elevated pressure.

Compounds of formula XIV can be prepared by reducing the nitro group in compounds of formula IX. There may be used as reducing agents, for example, iron (Bechamps reduction), tin(II) chloride, or hydrogen in the presence of a catalyst, such as Raney nickel or palladium on charcoal. The reaction conditions correspond to those given in the literature (for example Houben Weyl).

Compounds of the type

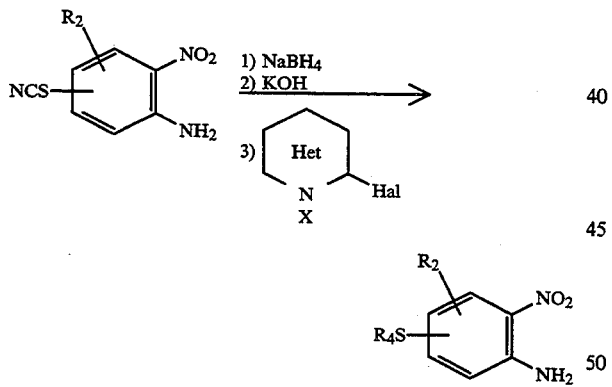

(IX, XIII and XIV)

can, when X=S, also be present in the dimeric form as a disulfide. The mercapto compounds can be obtained therefrom by reduction. Methods are known from the literature.

General reaction scheme 1

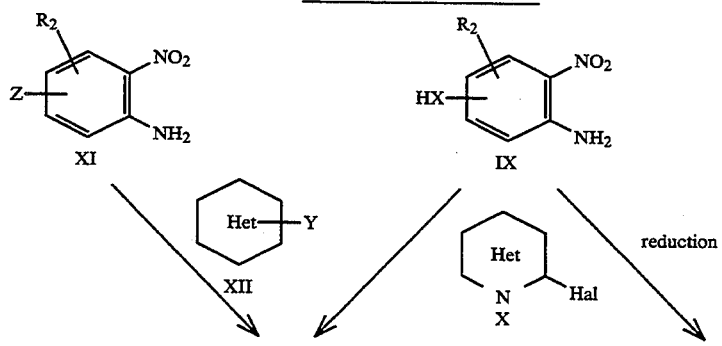

-continued
General reaction scheme 1

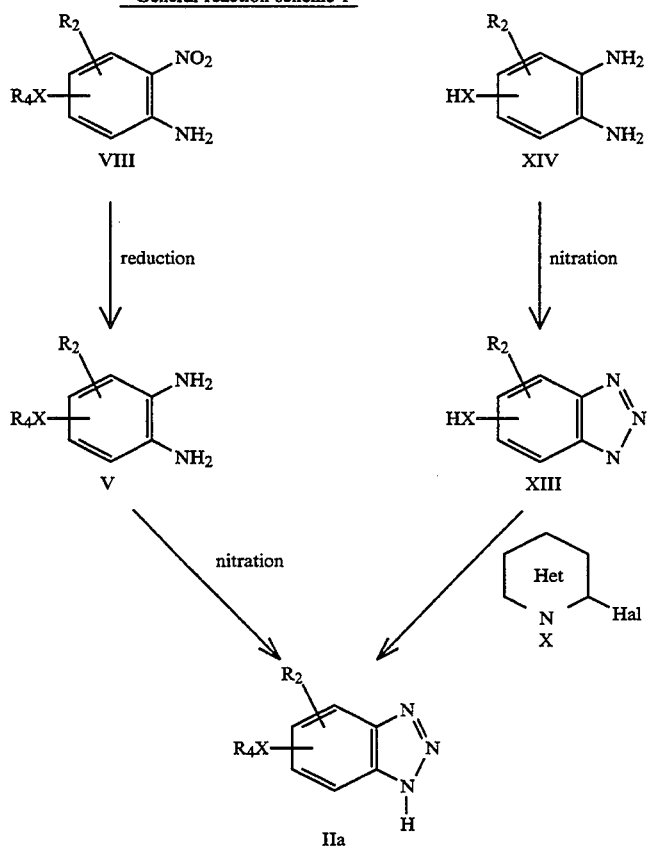

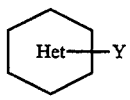 —Y = unsubstitutd or substituted hydroxypyridine, mercaptopyridine, hydroxypyrimidine, mercaptopyrimidine, hydroxypyrazine, mercaptopyrazine, hydroxypyridazine or mercaptopyridazine Z = leaving group (such as halogen) that is in the o- or p-position to the NO₂ group.

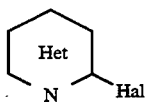 = unsubstituted or substituted 2-halopyridine, 2-halopyrazine, 2- or 4-halopyrimidine, 3-halopyridazine Compounds of formula II wherein M=H may also be prepared analogously to the processes described in EP-A-355 049 for compounds of formula IIa wherein R₂=H and R₃=substituted 2-pyridyloxy. Compounds of that type are also described in UK 2 157 679 and in EP-A-299 446.

If R₂ is fluorine, chlorine or bromine, the corresponding compounds may also be obtained by halogenating compounds wherein R₂ is hydrogen. That applies to compounds of formulae II, V, VI, VII, VIII, IX, XI, XIII and XIV.

Reaction conditions for the fluorination, chlorination and bromination are well known in chemical literature (e.g. Houben Weyl "Methoden der organischen Chemie").

Surprisingly, it has now been found that compounds of formula I have, for practical purposes, a very advantageous biocidal spectrum for the control of phytopathogenic microorganisms, especially fungi. They have very advantageous curative and preventive properties and are used for protecting numerous cultivated plants.

With the compounds of formula I it is possible to inhibit or destroy the pests which occur on plants or on parts of plants (fruit, blossoms, leaves, stems, tubers, roots) in different crops of useful plants, while at the same time the parts of plants which grow later are also protected, for example, against phytopathogenic fungi.

The novel compounds of formula I have proved especially effective against specific genera of the fungus class Fungi imperfecti (e.g. Cercospora), Basidiomycetes (e.g. Puccinia) and also Ascomycetes (e.g. Erysiphe and Venturia) and in particular against Oomycetes (e.g. Plasmopara, Peronospora, Pythium and Phytophthora). In plant protection they therefore represent a valuable addition to compositions for controlling phytopathogenic fungi. For practical application purposes they advantageously exhibit both curative and preventive properties and can be used for protecting numerous cultivated plants. With these compounds it is possible to inhibit or destroy the pests which occur on plants or on parts of plants (fruit, blossoms, leaves, stems, tubers, roots) in different crops of useful plants, while at the same time the parts of plants which grow later are also protected, for example, against phytopathogenic fungi. The compounds of formula I can also be used as dressing agents for protecting seeds (fruit, tubers, grains) and plant cuttings against fungus infections as well as against phytopathogenic fungi which occur in the soil.

The invention also relates to compositions comprising compounds of formula I as active ingredient, especially plant-protecting compositions, and to their use in the agricultural sector or related fields.

The present invention further embraces the preparation of those compositions, which comprises homogeneously mixing the active ingredient with one or more compounds or groups of compounds described herein. The invention furthermore relates to a method of treating plants, which comprises applying thereto the novel compounds of formula I or the novel compositions.

Target crops to be protected within the scope of the present invention comprise e.g. the following species of plants: cereals (wheat, barley, rye, oats, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (cucumber, marrows, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor) or plants such as tobacco, nuts, coffee, sugar cane, tea, peppers, vines, hops, bananas and natural rubber plants, as well as ornamentals.

The compounds of formula I are normally applied in the form of compositions and can be applied to the crop area or plant to be treated, simultaneously or in succession, with further compounds. These further compounds can be fertilisers or micronutrient donors or other preparations that influence plant growth. They can also be selective herbicides. insecticides, fungicides, bactericides, nematicides, molluscicicles or mixtures of several of these preparations, if desired together with further carriers, surfactants or other application-promoting adjuvants customarily employed in formulation technology.

Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers.

A preferred method of applying a compound of formula I, or an agrochemical composition which comprises at least one of said compounds, is foliar application. The number of applications and the rate of application depend on the risk of infestation by the corresponding pathogen. The compounds of formula I may also be applied to seeds (coating) either by impregnating the seeds with a liquid formulation comprising the active ingredient, or coating them with a solid formulation.

The compounds of formula I are used in unmodified form or, preferably, together with the adjuvants conventionally employed in formulation technology and are for this purpose advantageously formulated in known manner e.g. into emulsifiable concentrates, coatable pastes, directly sprayable or dilutable solutions, dilute emulsions, wettable powders, soluble powders, dusts, granules and also encapsulations in e.g. polymer substances. As with the nature of the compositions, the methods of application, such as spraying, atomising, dusting, scattering, coating or pouring, are chosen in accordance with the intended objectives and the prevailing circumstances.

Advantageous rates of application are normally from 5 g to 2 kg of active ingredient (a.i.) per hectare (ha), preferably from 10 g to 1 kg a.i./ha, especially from 20 g to 600 g a.i./ha.

The formulations, i.e. the compositions, preparations or mixtures comprising the compound (active ingredient) of formula I and, where appropriate, a solid or liquid adjuvant, are prepared in known manner, e.g. by homogeneously mixing and/or grinding the active ingredient with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils, such as epoxidised coconut oil or soybean oil; and water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carders are porous types, for example pumice, broken brick, sepiolite or bentonite; and suitable non-sorbent carriers are, for example, calcite or sand. In addition, a great number of pregranulated materials of inorganic or organic nature can be used, e.g. dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and water-soluble synthetic surface-active compounds are suitable anionic surfactants.

Representative examples of non-ionic surfactants are nonylphenolpolyethoxyethanols, castor oil polyglycol ethers, polypropylene/polyethylene oxide adducts, tributylphenoxypolyethyleneethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals.

Further surfactants customarily employed in formulation technology are known to the person skilled in the art or can be found in the relevant specialist literature.

The agrochemical compositions usually comprise 0.1 to 99% by weight, preferably 0.1 to 95% by weight, of a compound of formula I, 99.9 to 1% by weight, preferably 99.8 to 5% by weight, of a solid or liquid adjuvant, and 0 to 25% by weight, preferably 0.1 to 25% by weight, of a surfactant.

Whereas commercial products will preferably be formulated as concentrates, the end user will normally employ dilute formulations.

The compositions may also comprise further auxiliaries such as stabilisers, antifoams, viscosity regulators, binders or tackifiers, as well as fertilisers or other active ingredients for obtaining special effects.

The Examples that follow illustrate the invention described above without limiting the scope thereof in any way. Temperatures are given in degrees Celsius.

PREPARATION EXAMPLES

P-1. Preparation of 1(3)-methylsulfonyl-5-chloro-6-(5-chloro-6-ethylpyrimid-4-yloxy)-benzotriazole of the formula

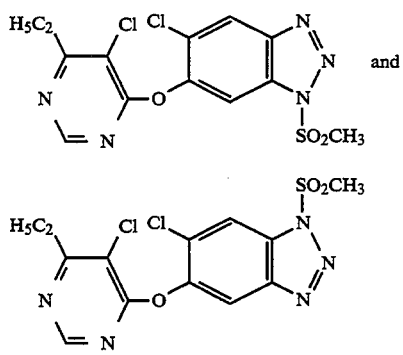

Preparation of the Intermediates a) Preparation of 5-chloro-6-ethyl-3-(2-chloro-4-nitro-5-aminophenoxy)-pyrimidine.

6.8 g of potassium hydroxide are added to a solution of 15.0 g of 2-chloro-4-amino-5-nitrophenol in 100 ml of dimethylsulfoxide and the reaction mixture is stirred at room temperature for 30 min. A solution of 15.5 g of 4,5-dichloro-6-ethylpyrimidine in 30 ml of dimethyl sulfoxide is added thereto and the reaction mixture is stirred for 90 minutes at 75° C. The reaction solution is poured onto water, the pH is adjusted with 5N hydrochloric acid to pH=4 and the mixture is extracted with ethyl acetate. The organic phase is washed with concentrated NaCl solution (brine), dried over magnesium sulfate and concentrated. Chromatography on silica gel with hexane/diethyl ether (60/40) yields 16.3 g of intermediate a).

b) Preparation of 5-chloro-6-ethyl-3-(2-chloro-4,5-diaminophenoxy)-pyrimidine

A suspension of 15.3 g of the intermediate obtained under a) with 3 g of Raney nickel in 160 ml of tetrahydrofuran is stirred at room temperature for 8 hours in a hydrogen atmosphere. The mixture is filtered over Celite and concentrated, yielding 13.6 g of intermediate b), m.p. 160°-165° C.

c) Preparation of 5-chloro-6-(5-chloro-6-ethylpyrimid-4-yloxy)-benzotriazole.

A solution of 13.2 g of intermediate b) in 50 ml of glacial acetic acid is added dropwise in the course of 30 minutes to an ice-cooled solution of sodium nitrite. The resulting suspension is stirred for 10 hours at room temperature to complete the reaction and is filtered. The filter residue is washed with water, dissolved in ethyl acetate, dried over magnesium sulfate and concentrated, yielding 12.7 g of intermediate c), m.p. 149°-151° C.

d) Preparation of the isomeric mixture of the end product, Compound no. 1.124

1.4 g of potassium hydroxide is added to a solution of 5.8 g of intermediate c) in 100 ml of acetone and the reaction mixture is stirred for 1 hour. 3.2 g of methylsulfonyl chloride in 30 ml of acetone are added thereto and the mixture is stirred overnight. After the addition of 1 ml of triethylamine, the suspension is stirred for a further 1 hour at room temperature, then filtered through Celite and the filtrate is concentrated. The concentrate is dissolved in dichloromethane, 5 g of silica gel are added and the reaction mixture is stirred for five minutes at room temperature. Silica gel is filtered off and the solvent is evaporated. Recrystallisation from diethyl ether yields 5.6 g of the structural isomers, m.p. 137°-140° C.

P-2. Preparation of 1(3)-methylsulfonyl-5-chloro-6-(3-chloro-5-trifluoromethyl-pyrid-2-ylthio)-benzotriazole of the formula

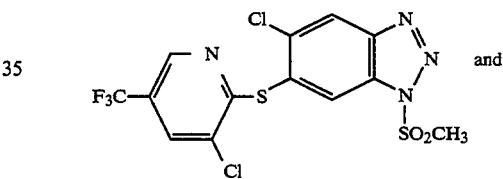

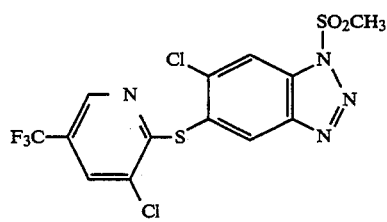

Preparation of the Intermediates a) Preparation of 2-nitro-4-chloro-5-mercapto-aniline.

50.0 g of 2-nitro-4,5-dichloro-aniline are dissolved in 250 ml of water and 250 ml of ethanol, 59.0 g of $Na_2S \cdot 8H_2O$ are added and the reaction mixture is boiled for 2.5 hours under reflux. After cooling to room temperature, 1 liter of water is added to the reaction solution which is then filtered and rendered acidic by the addition of 25 ml of acetic acid. The yellow precipitate is filtered off, washed with water and dried, yielding 32.6 g of compound a) (m.p. 183° C., decomposition).

b) Preparation of 4-chloro-5-mercapto-o-phenylenediamine.

255 g of compound a) are dissolved in 3 liters of tetrahydrofuran, 255 g of platinum (5%) on charcoal are added and the reaction mixture is hydrogenated for 83 hours under a hydrogen atmosphere. The catalyst is filtered off and the solution is concentrated, yielding 163 g of intermediate b), m.p. 158°–160° C.

c) Preparation of 1,2-bis(5-chloro-benzotriazol-6-yl) disulfide.

50.0 g of compound b) are dissolved in 350 ml of acetic acid and added dropwise at 0°–5° C. to a solution of 43.5 g of sodium nitrite in 1.75 liters of water. The resulting suspension is stirred for 18 hours at room temperature. Filtration, washing with water and drying are carried out, yielding 48.5 g of compound c) having an m.p. of >250° C.

d) Preparation of 5-chloro-6-mercapto-benzotriazole.

43.9 g of Na2S204 and 28.2 g of K2CO3 are added to 35.7 g of compound c) suspended in 250 ml of water and the reaction mixture is boiled under reflux for 1 hour. The resulting brown solution is filtered and acidified with hydrochloric acid. The precipitate is filtered off and dried, yielding 27.8 g of compound d), m.p. 204°–207° C.

e) Preparation of 5-chloro-6-(3-chloro-5-trifluoromethyl-pyrid-2-ylthio)-benzomazole.

4.8 g of 2,3-dichloro-5-trifluoromethylpyridine and 4.1 ml of triethylamine are added to 4.0 g of compound d) suspended in 30 ml of n-propanol and the reaction mixture is stirred for 18 hours at 70° C. The mixture is poured onto hydrochloric acid, extracted with ethyl acetate, dried over sodium sulfate, filtered and concentrated. Chromatography on silica gel with methylene chloride/ethanol 9:1 as eluant yields 4.0 g of compound e), m.p. 222°–223° C.

f) Preparation of the isomeric mixture of the end product, Compound no. 2.161

0.7 g of KOH is added to 3.5 g of intermediate e) dissolved in 35 ml of acetone. After stirring for 2 hours at room temperature, 1.1 ml of methylsulfonylchloride are added and the reaction mixture is stirred overnight. The suspension is then filtered and the solution is concentrated. The concentrate is dissolved in dichloromethane, 5 g of silica gel are added and the reaction mixture is stirred for 20 minutes at room temperature. The silica gel is filtered off and the solution is concentrated. Digestion with diethyl ether and drying of the crystals yield 2.7 g of the structural isomers, m.p. 167°–168° C.

P-3. Preparation of 1-methylsulfonyl-4-bromo-6-(6-methoxy-pyridazin-3-yloxy)-benzotriazole triazole (Comp. No. 3.178)

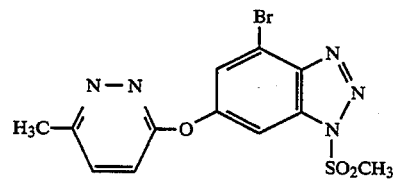

0.45 g (1.40 mmol) of 6-(4-methoxy-2,3-pyridazinyloxy)-4-bromo-benzotriazole is suspended in 10 ml of acetone and, at room temperature, 0.58 g (4.19 mmol) of anhydrous potassium carbonate and 0.32 g (2.8 mmol) of methylsulfonyl chloride are added in succession thereto. The suspension is then stirred for 10 minutes at room temperature. For working-up, the reaction mixture is cooled in an ice bath and 10–20 ml of ice-water are added thereto. The crystals that are obtained are filtered off, washed in succession with water and diethyl ether and dried under a high vacuum at 40° C., yielding 0.45 g (80% of the theoretical yield) of product in the form of beige crystals having a melting point, with decomposition, of 187°–188° C. (uncorr.).

The following compounds of formula I can be prepared in that manner or in the manner one of the process variants described hereinbefore.

TABLE 1

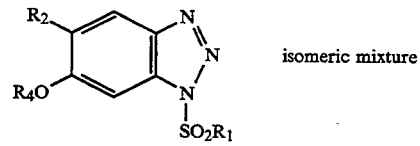

isomeric mixture

| Comp. No. | $R_1$ | $R_2$ | $R_4$ | m.p. |
|---|---|---|---|---|
| 1.1 | $CH_3$ | H | 2-pyridyl | |
| 1.2 | Et | Cl | 2-pyridyl | |
| 1.3 | i-Pr | Br | 2-pyridyl | |
| 1.4 | $N(CH_3)_2$ | F | 2-pyridyl | |
| 1.5 | $CH_3$ | $CH_3$ | 3-pyridyl | |
| 1.6 | $CH_3$ | Cl | 4-pyridyl | |
| 1.7 | $CH_3$ | $CH_3O$ | 3-Cl-2-pyridyl | |
| 1.8 | i-Pr | $CF_3$ | 3-Cl-2-pyridyl | |
| 1.9 | $CF_3$ | $OCF_3$ | 4-Cl-2-pyridyl | |
| 1.10 | $CH_3$ | Cl | 4-Cl-2-pyridyl | |
| 1.11 | $N(CH_3)_2$ | H | 5-Cl-2-pyridyl | |
| 1.12 | $CH_3$ | Br | 5-Cl-2-pyridyl | |
| 1.13 | $CH_3$ | $C_2H_5$ | 6-Cl-2-pyridyl | |
| 1.14 | Bu | n-$C_4H_9$ | 4-Br-2-pyridyl | |
| 1.15 | $CH_3$ | $N(CH_3)_2$ | 4-Br-2-pyridyl | |
| 1.16 | $CH_3$ | Cl | 3-F-2-pyridyl | |
| 1.17 | $CH_3$ | Br | 3-$CF_3$-2-pyridyl | |
| 1.18 | $CH_3$ | On-$C_4H_9$ | 4-$CF_3$-2-pyridyl | |
| 1.19 | $N(CH_3)_2$ | H | 5-$CF_3$-2-pyridyl | 58–63° C. |
| 1.20 | $CH_3$ | H | 5-$CF_3$-2-pyridyl | 127–130° C. |
| 1.21 | $CH_3$ | H | 6-$CF_3$-2-pyridyl | 105–109° C. |
| 1.22 | $CH_3$ | $OCF_2H$ | 3-$C_6F_{13}$-2-pyridyl | |
| 1.23 | i-Pr | $OC_2F_5$ | 3-$CH_3$-2-pyridyl | |
| 1.24 | $CH_3$ | Cl | 5-$CF_3$-2-pyridyl | 131–144° C. |
| 1.25 | n-$C_4H_9$ | n-$C_4F_9$ | 4-$CH_3$-2-pyridyl | |
| 1.26 | $CH_3$ | Cl | 4-$CH_3$-2-pyridyl | |

TABLE 1-continued

[Structure: benzotriazole with R2 at 5-position, R4O at 6-position, SO2R1 on N1; isomeric mixture]

| Comp. No. | R₁ | R₂ | R₄ | m.p. |
|---|---|---|---|---|
| 1.27 | CH₃ | Br | 5-CH₃-2-pyridyl | |
| 1.28 | CH₃ | H | 6-CH₃-2-pyridyl | |
| 1.29 | CH₃ | On-C₄H₉ | 3-i-Pr-2-pyridyl | |
| 1.30 | CH₃ | N(n-C₄H₉)₂ | 4-n-Hex-2-pyridyl | |
| 1.31 | CH₃ | F | 5-Et-2-pyridyl | |
| 1.32 | CH₃ | H | 3-OCH₂-2-pyridyl | |
| 1.33 | CH₃ | Br | 4-OCH₃-2-pyridyl | |
| 1.34 | CH₃ | I | 5-OMe-2-pyridyl | |
| 1.35 | CH₃ | i-C₃H₇ | 6-OMe-2-pyridyl | |
| 1.36 | CH₃ | OC₂H₅ | 4-OEt₂-2-pyridyl | |
| 1.37 | CH₃ | N(CH₃(C₂H₅) | 4-Oi-Pr-2-pyridyl | |
| 1.38 | CH₃ | OCF₃ | 3-On-Hex-2-pyridyl | |
| 1.39 | N(CH₃)₂ | CF₃ | 5-Ot-Bu-2-pyridyl | |
| 1.40 | CH₃ | Cl | 3-OCF₃-2-pyridyl | |
| 1.41 | CH₃ | tert-C₄H₉ | 4-OCF₃-2-pyridyl | |
| 1.42 | CH₃ | H | 5-OCF₃-2-pyridyl | |
| 1.43 | CH₃ | H | 6-OCF₃-2-pyridyl | |
| 1.44 | CH₃ | Otert-C₄H₉ | 3-OCHF₂-2-pyridyl | |
| 1.45 | CH₃ | H | 4-OCHF₂-2-pyridyl | |
| 1.46 | CH₃ | Cl | 5-OCHF₂-2-pyridyl | |
| 1.47 | CH₃ | H | 6-OCHF₂-2-pyridyl | |
| 1.48 | CH₃ | Br | 6-OCH₂CF₃-2-pyridyl | |
| 1.49 | CH₃ | C₂H₅ | 6-OC₆F₁₃-2-pyridyl | |
| 1.50 | CH₃ | Oi-C₃H₇ | 6-NO₂-2-pyridyl | |
| 1.51 | CH₃ | On-C₄H₉ | 4-NO₂-2-pyridyl | |
| 1.52 | Et | Cl | 3-NO₂-2-pyridyl | |
| 1.53 | N(CH₃)₂ | H | 5-NO₂-2-pyridyl | |
| 1.54 | CH₃ | Br | 6-SMe-2-pyridyl | |
| 1.55 | CH₃ | OCF₃ | 6-S-hexyl-2-pyridyl | |
| 1.56 | CH₃ | H | 4-SMe-2-pyridyl | |
| 1.57 | CH₃ | CH₂CF₃ | 6-SiPr-2-pyridyl | |
| 1.58 | CH₃ | Cl | 3-COOMe-2-pyridyl | |
| 1.59 | i-Pr | H | 5-COOBu-2-pyridyl | |
| 1.60 | CH₃ | CF₃ | 5-COOMe-2-pyridyl | |
| 1.61 | CH₃ | Cl | 6-COOiPr-2-pyridyl | |
| 1.62 | CH₃ | Oi-C₃H₇ | 5-CN-2-pyridyl | |
| 1.63 | CH₃ | Cl | 6-CN-2-pyridyl | |
| 1.64 | CH₃ | Br | 4-N(CH₃)₂-2-pyridyl | |
| 1.65 | CH₃ | OCF₃ | 3-N(Bu)₂-2-pyridyl | |
| 1.66 | CH₃ | H | 6-N(i-Pr)₂-2-pyridyl | |
| 1.67 | CH₃ | N(CH₃)₂ | 4-N(CH₃)(Et)-2-pyridyl | |
| 1.68 | CH₃ | Cl | 3,5-(Cl)₂-2-pyridyl | 124–135° C. |
| 1.69 | CH₃ | H | 3-Cl,5-F-2-pyridyl | |
| 1.70 | CH₃ | OCH₃ | 3,4,5,6(Cl)₄-2-pyridyl | |
| 1.71 | CH₃ | CH₃ | 3-CF₃,5-Cl-2-pyridyl | |
| 1.72 | CH₃ | H | 3-Cl,5-,CF₃-2-pyridyl | 147–150° C. |
| 1.73 | CH₃ | Oi-C₃H₇ | 6-Cl-3-CF₃-2-pyridyl | |
| 1.74 | CH₃ | Cl | 3-pyridazinyl | |
| 1.75 | CH₃ | H | 6-Cl-3-pyridazinyl | |
| 1.76 | nBu | OCF₃ | 6-Br-4-CF₃-2-pyridyl | |
| 1.77 | CH₃ | N(CH₃)₂ | 4-Cl,3-CH₃-2-pyridyl | |
| 1.78 | CH₃ | OCF₃ | 6-Cl-5-CH₃-2-pyridyl | |
| 1.79 | CH₃ | CH₃ | 4-Br-5-CH₃-2-pyridyl | |
| 1.80 | CH₃ | Cl | 6-CH₃-4-CF₃-2-pyridyl | |
| 1.81 | CH₃ | H | 3-CH₃-4-Br-2-pyridyl | |
| 1.82 | CH₃ | Cl | 4,6-(CH₃)₂-3-CN-2-pyridyl | |
| 1.83 | CH₃ | Cl | 6-(CH₃)-4-(COOEt)-3-CN-2-pyridyl | |
| 1.84 | CH₃ | H | 2-Br-3-pyridyl | |
| 1.85 | CH₃ | Br | 2-Cl-3-pyridyl | |
| 1.86 | CH₃ | n-C₄H₉ | 2-I,6-CH₃-3-pyridyl | |
| 1.87 | CH₃ | OCH₃ | 5-Cl-3-pyridyl | |
| 1.88 | Et | Cl | 2,6(Br₂)-3-pyridyl | |
| 1.89 | CH₃ | H | 6(CH₃)-3-pyridyl | |
| 1.90 | CH₃ | Otert-C₄H₉ | 2-NO₂-3-pyridyl | |
| 1.91 | CH₃ | i-C₃H₇ | 2-NO₂-6-CH₃-3-pyridyl | |
| 1.92 | CH₃ | N(CH₃)₂ | 2-[N(CH₃)₂]-3-pyridyl | |
| 1.93 | CH₃ | n-C₄H₉ | 2-COOMe-3-pyridyl | |
| 1.94 | CH₃ | Cl | 5-CF₃-3-pyridyl | |
| 1.95 | CH₃ | H | 2,3,5,6-(Cl₄)-4-pyridyl | |
| 1.96 | CH₃ | Cl | 3,5-Cl₂-4-pyridyl | |
| 1.97 | CH₃ | CH₃ | 2-CH₃-4-pyridyl | |
| 1.98 | CH₃ | Br | 2-COOMe-4-pyridyl | |

TABLE 1-continued

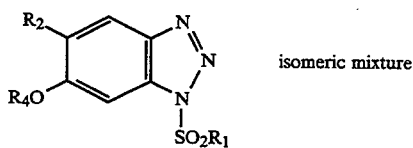

isomeric mixture

| Comp. No. | $R_1$ | $R_2$ | $R_4$ | m.p. |
|---|---|---|---|---|
| 1.99 | Et | sec-$C_4H_9$ | 2-Br-4-pyridyl | |
| 1.100 | $N(CH_3)_2$ | F | 2-Cl-4-pyridyl | |
| 1.101 | $CH_3$ | H | 2-$CF_3$-4-pyridyl | |
| 1.102 | $CH_3$ | H | 2-pyrimidyl | |
| 1.103 | $CH_3$ | $CF_3$ | 4-pyrimidyl | |
| 1.104 | $CH_3$ | $OCH_3$ | 5-pyrimidyl | |
| 1.105 | $CH_3$ | Br | 4-$CH_3$-2-pyrimidyl | |
| 1.106 | $CH_3$ | Cl | 4,6-$(CH_3)_2$-2-pyrimidyl | 63–67° C. |
| 1.107 | $N(CH_3)_2$ | H | 4,6-$(CH_3)_2$-2-pyrimidyl | |
| 1.108 | $CH_3$ | O$i$-$C_3H_7$ | 4-Cl-2-pyrimidyl | |
| 1.109 | $CH_3$ | Cl | 4,6-$(Cl)_2$-2-pyrimidyl | |
| 1.110 | $CH_3$ | H | 4,5,6$(Cl)_3$-2-pyrimidyl | |
| 1.111 | $CH_3$ | $CF_3$ | 4-Cl-6-$CH_3$-2-pyrimidyl | |
| 1.112 | $CH_3$ | $OCF_3$ | 4-$CF_3$-5,6-$F_2$-2-pyrimidyl | |
| 1.113 | Et | Cl | 4-$N(CH_3)_2$-5-$NO_2$-6-$CH_3$-2-pyrimidyl | |
| 1.114 | $CH_3$ | $OCF_2$—$CF_2$H | 4-$(CH_3)$-6$(OCH_3)$-2-pyrimidyl | |
| 1.115 | $CH_3$ | Cl | 4,6-$F_2$-2-pyrimidyl | |
| 1.116 | $CH_3$ | Br | 4-$(CF_3)$-5-COOMe-2-pyrimidyl | |
| 1.117 | Bu | $N(CH_3)_2$ | 4-$N(Bu)_2$-5-F-2-pyrimidyl | |
| 1.118 | $CH_3$ | H | 4-$OC_4F_9$-2-pyrimidyl | |
| 1.119 | $CH_3$ | Cl | 4-(Cl)-5-$(CH_3)$-2-pyrimidyl | 175–177° C. |
| 1.120 | $CH_3$ | H | 4,6-$(OMe)_2$-2-pyrimidyl | |
| 1.121 | $CH_3$ | H | 2,6-$Cl_2$-1-pyrimidyl | |
| 1.122 | $CH_3$ | Cl | 2-Cl,6-$CH_3$-4-pyrimidyl | |
| 1.123 | i-Pr | Br | 2-Cl-5-$CH_3$-4-pyrimidyl | |
| 1.124 | $CH_3$ | Cl | 5-Cl-6-Et-4-pyrimidyl | 137–140° C. |
| 1.125 | $CH_3$ | Cl | 2,6-$(MeO)_2$-4-pyrimidyl | 159–160° C. |
| 1.126 | $CH_3$ | Cl | 2-Cl,5-F-4-pyrimidyl | |
| 1.127 | $CH_3$ | $OCF_3$ | 2,5-$F_2$-6-$CF_3$-4-pyrimidyl | |
| 1.128 | $CH_3$ | i-$C_3H_7$ | 2-Cl-6-$N(CH_3)_2$-4-pyrimidyl | |
| 1.129 | $CH_3$ | F | 2,6-$F_2$-4-pyrimidyl | |
| 1.130 | $CH_3$ | Cl | 2-SMe-6-Me-4-pyrimidyl | |
| 1.131 | $CH_3$ | H | 2-S-Pr-4-pyrimidyl | |
| 1.132 | $CH_3$ | Cl | 2-Cl-4-pyrimidyl | |
| 1.133 | $CH_3$ | $OCH_3$ | 2-SMe-6-Cl-4-pyrimidyl | |
| 1.134 | Bu | O$n$-$C_3H_7$ | 2-$CH_3$,4-SMe,5-CN-4-pyrimidyl | |
| 1.135 | $CH_3$ | H | 2-$CH_2$-5-pyrimidyl | |
| 1.136 | $CH_3$ | Cl | 4-Cl-5-pyrimidyl | |
| 1.137 | $CH_3$ | $CH_3$ | 2-SBu-5-pyrimidyl | |
| 1.138 | $CH_3$ | $OCF_3$ | 2-CN-4-$NO_2$-5-pyrimidyl | |
| 1.139 | $CH_3$ | N($n$-$C_4H_9$)$_2$ | 2-MeO-5-pyrimidyl | |
| 1.140 | $N(CH_3)_2$ | H | 2-COOMe-5-pyrimidyl | |
| 1.141 | $CH_3$ | Cl | 4-$N(Bu)_2$-5-pyrimidyl | |
| 1.142 | $CH_3$ | Cl | 2,4-$Cl_2$-5-pyrimidyl | |
| 1.143 | $CH_3$ | $CF_3$ | 2,4-$Cl_2$-5-pyrimidyl | |
| 1.144 | $CH_3$ | Cl | 2-pyrazinyl | 195–196° C. |
| 1.145 | $CH_3$ | Cl | 3-chloro-2-pyrazinyl | 149–152° C. |
| 1.146 | $CH_3$ | Br | 6-chloro-2-pyrazinyl | |
| 1.147 | $CH_3$ | Cl | 3,6-$Me_2$-2-pyrazinyl | |
| 1.148 | $CH_3$ | $CF_3$ | 3-Cl-5-$N(Me)_2$-6-COOMe-2-pyrazinyl | |
| 1.149 | $N(CH_3)_2$ | $CH_3$ | 3,5-$(NBu_2)_2$-6-CN-2-pyrazinyl | |
| 1.150 | Bu | $OCH_3$ | 3,5,6-$(CH_3)_3$-2-pyrazinyl | |
| 1.151 | $CH_3$ | $OCF_2H$ | 3-Et-2-pyrazinyl | |
| 1.152 | $CH_3$ | Cl | 5-OMe-2-pyrazinyl | |
| 1.153 | $CH_3$ | Br | 6-Br-2-pyrazinyl | |
| 1.154 | $CH_3$ | H | 5-OMe-2-pyrazinyl | |
| 1.155 | $CH_3$ | Cl | 3-$NO_2$-2-pyrazinyl | |
| 1.156 | $CH_3$ | H | 3,5-$(Cl)_2$-2-pyridyl | 126–128° C. |
| 1.157 | $N(CH_3)_2$ | H | 3,5$(Cl)_2$-2-pyridyl | $n_D^{20}$ = 1.5800 |
| 1.158 | $CH_3$ | H | 3-F,5Cl-2-pyridyl | 109–112° C. |
| 1.159 | $N(CH_3)_2$ | H | 3-F,5Cl-2-pyridyl | 114–115° C. |
| 1.160 | $CH_3$ | F | 3-Cl,5($CF_3$)-2-pyridyl | |
| 1.161 | $CH_3$ | Cl | 3-Cl,5($CF_3$)-2-pyridyl | 135–137° C. |
| 1.162 | $CH_3$ | Br | 3-Cl,5($CF_3$)-2-pyridyl | 139–144° C. |
| 1.163 | $CH_3$ | Cl | 4,6($OCH_3$)$_2$-2-pyrimidyl | |
| 1.164 | $CH_3$ | Br | 4,6($OCH_3$)$_2$-2-pyrimidyl | |
| 1.165 | $CH_3$ | Cl | 5-Cl,6-$OCH_3$-2-pyrimidyl | 185–190° C. |
| 1.166 | $N(CH_3)_2$ | Cl | 3-F,5-Cl-2-pyridyl | 149–153° C. |
| 1.167 | $CH_3$ | H | 5-Cl-6-n-propyl-4-pyrimidyl | 120–126° C. |
| 1.168 | $N(CH_3)_2$ | H | 5-Cl-6-n-propyl-4- | resin |

TABLE 1-continued $R_2$, $R_4O$, $SO_2R_1$ substituted benzotriazole, isomeric mixture

| Comp. No. | $R_1$ | $R_2$ | $R_4$ | m.p. |
|---|---|---|---|---|
| | | | pyrimidyl | |
| 1.169 | N(CH$_3$)$_2$ | Cl | 5-Cl-6-CH$_3$-4-pyrimidyl | 110–112° C. |
| 1.170 | CH$_3$ | Cl | 5-Cl-6-CH$_3$-4-pyrimidyl | 146–150° C. |
| 1.171 | N(CH$_3$)$_2$ | Cl | 5-CH$_3$-6-Cl-2-pyrimidyl | 128–134° C. |
| 1.172 | CH$_3$ | Cl | 5-CH$_3$-6-Cl-2-pyrimidyl | 175–177° C. |
| 1.173 | N(CH$_3$)$_2$ | H | 5-Cl-6-CH$_3$-4-pyrimidyl | resin |
| 1.174 | CH$_3$ | Cl | 4-CH$_3$-6-cycl.propyl-2-pyrimidyl | 162–166° C. |
| 1.175 | N(CH$_3$)$_2$ | Cl | 2-i-propyl-5-Cl-6-CH$_3$-2-pyrimidyl | resin |
| 1.176 | CH$_3$ | Cl | 6-CF$_3$-4-pyrimidyl | 120–124° C. |
| 1.177 | CH$_3$ | Cl | 2-i-propyl-5-Cl-6-CH$_3$-4-pyrimidyl | 147–150° C. |
| 1.178 | N(CH$_3$)$_2$ | Cl | 6-CF$_3$-4-pyrimidyl | 141–145° C. |
| 1.179 | CH$_3$ | H | 5-Cl-6-CH$_3$-4-pyrimidyl | 138–142° C. |
| 1.180 | CH$_3$ | CH$_3$ | 3-Cl-5-CF$_3$-pyridyl | 144–146° C. |
| 1.181 | CH$_3$ | OCH$_3$ | 3-Cl-5-CF$_3$-pyridyl | 130–135° C. |
| 1.182 | CH$_3$ | H | 5-CF$_3$-6-Cl-pyridyl | 128–135° C. |
| 1.183 | N(CH$_3$)$_2$ | H | 5-CF$_3$-6-Cl-pyridyl | 121–128° C. |
| 1.184 | N(CH$_3$)$_2$ | CF$_3$ | 3-Cl-5-CF$_3$-pyridyl | 153–156° C. |
| 1.185 | CH$_3$ | Cl | 5-Cl-2-pyridyl | 98–102° C. |
| 1.186 | CH$_3$ | H | 4-CF$_3$-2-pyridyl | oil |
| 1.187 | N(CH$_3$)$_2$ | H | 3-Cl-2-pyrazinyl | 97–99° C. |
| 1.188 | N(CH$_3$)$_2$ | H | 3-CF$_3$-5-Cl-2-pyridyl | 120–129° C. |
| 1.189 | N(CH$_3$)$_2$ | H | 3-CF$_3$-5-Cl-2-pyridyl | solid |
| 1.190 | CH$_3$ | Cl | 3-CF$_3$-5-Cl-2-pyridyl | 154–155° C. |
| 1.191 | N(CH$_3$)$_2$ | H | 4-CF$_3$-6-CH$_3$-2-pyridyl | resin |
| 1.192 | N(CH$_3$)$_2$ | H | 5-Cl-6-ethyl-4-pyrimidyl | 104–105° C. |
| 1.193 | CH$_3$ | H | 3-Cl-2-pyrazine | 141–142° C. |
| 1.194 | N(CH$_3$)$_2$ | H | 6-CF$_3$-2-pyridyl | 133–135° C. |
| 1.195 | CH$_3$ | H | 4-CF$_3$-2-pyridyl | 80–82° C. |
| 1.196 | N(CH$_3$)$_2$ | H | 3-CF$_3$-2-pyridyl | 119–121° C. |
| 1.197 | CH$_3$ | H | 6-Cl-2-pyridyl | 98–100° C. |
| 1.198 | CH$_3$ | H | 5-Cl-6-ethyl-4-pyrimidyl | 144–145° C. |
| 1.199 | CH$_3$ | H | 4-CF$_3$-6-CH$_3$-2-pyridyl | 88.5–100° C. |
| 1.200 | CH$_3$ | H | 3-CF$_3$-2-pyridyl | 182–185° C. |
| 1.201 | N(CH$_3$)$_2$ | Br | 3-Cl-5-CF$_3$-2-pyridyl | 109–111° C. |
| 1.202 | CH$_3$ | H | 3-CF$_3$-5-Cl-2-pyridyl | 101–102° C. |
| 1.203 | CH$_3$ | Cl | 5-Cl-6-CH$_3$-2-CH$_3$-4-pyrimidyl | |
| 1.204 | CH$_3$ | Cl | 4-CH$_3$-5-Cl-6-CH$_3$-2-pyrimidyl | |
| 1.205 | CH$_3$ | Cl | 6-OCH$_3$-2-pyrimidyl | |
| 1.206 | CH$_3$ | Cl | 4-CH$_3$-5-S-ethyl-6-CH$_3$-2-pyrimidyl | 125–126° C. |
| 1.207 | CH$_3$ | H | 6-CF$_3$-2-pyridyl | 124–125° C. |
| 1.208 | CH$_3$ | Cl | 5-CF$_3$-2-pyridyl | 163–164° C. |
| 1.209 | CH$_3$ | Cl | 3-Cl-5-CF$_3$-2-pyridyl | 153–155° C. |
| 1.210 | CH$_3$ | Br | 3-Cl-5-CF$_3$-2-pyridyl | 177–178° C. |
| 1.211 | CH$_3$ | Cl | 2,6-(OCH$_3$)$_2$-4-pyrimidyl | 159–160° C. |
| 1.212 | CH$_3$ | Cl | 2,6-(CH$_3$)$_2$-4-pyrimidyl | 63–67° C. |
| 1.213 | CH$_3$ | H | 2,6-(OCH$_3$)$_2$-4-pyrimidyl | |
| 1.214 | CH$_3$ | H | 6-Cl-2-pyrazinyl | |
| 1.215 | CH$_3$ | H | 3-ethyl-2-pyrazinyl | |
| 1.216 | CH$_3$ | H | 6-CH$_3$-3-pyridazinyl | |
| 1.217 | CH$_3$ | H | 6-OCH$_3$-3-pyridazinyl | |
| 1.218 | CH$_3$ | H | 6-OCH$_3$-3-pyridazinyl | |
| 1.219 | CH$_3$ | H | 4,5-Cl$_2$-3-pyridazinyl | |
| 1.220 | N(CH$_3$)$_2$ | H | 3-COOEt-2-pyridyl | 139–140° C. |
| 1.221 | N(CH$_3$)$_2$ | Cl | 6-OCH$_3$-4-Pyrimidyl | 135–144° C. |
| 1.222 | N(CH$_3$)$_2$ | Cl | 4-CH$_3$-5-S-Ethyl-6-CH$_3$-2-Pyrimidyl | 97–98° C. |
| 1.223 | N(CH$_3$)$_2$ | Cl | 3,5-Cl$_2$-2-Pyridyl | 125–127° C. |

TABLE 2

Structure: benzotriazole with $R_2$ and $R_4S$ substituents on benzene ring, and $SO_2R_1$ on N1 (mixture of isomers)

| Comp. No. | $R_1$ | $R_2$ | $R_4$ | m.p. |
|---|---|---|---|---|
| 2.1 | CH$_3$ | H | 2-pyridyl | 116–118° C. |
| 2.2 | Et | Cl | 2-pyridyl | |
| 2.3 | n-Pr | Br | 2-pyridyl | |
| 2.4 | N(CH$_3$)$_2$ | F | 3-pyridyl | |
| 2.5 | CH$_3$ | CH$_3$ | 3-pyridyl | |
| 2.6 | CH$_3$ | Cl | 4-pyridyl | 173–176° C. |
| 2.7 | CH$_3$ | CH$_3$O | 3-Cl-2-pyridyl | |
| 2.8 | CH$_3$ | CF$_3$ | 3-Cl-2-pyridyl | |
| 2.9 | CF$_3$ | OCF$_3$ | 4-Cl-2-pyridyl | |
| 2.10 | CH$_3$ | Cl | 4-Cl-2-pyridyl | |
| 2.11 | N(CH$_3$)$_2$ | H | 5-Cl-2-pyridyl | |
| 2.12 | CH$_3$ | F | 5-Cl-2-pyridyl | |
| 2.13 | CH$_3$ | C$_2$H$_5$ | 6-Cl-2-pyridyl | |
| 2.14 | CH$_3$ | n-C$_4$H$_9$ | 4-Br-2-pyridyl | |
| 2.15 | CH$_3$ | N(CH$_3$)$_2$ | 4-Br-2-pyridyl | |
| 2.16 | CH$_3$ | Cl | 3-F-2-pyridyl | |
| 2.17 | N(Et)$_2$ | Br | 3-CF$_3$-2-pyridyl | |
| 2.18 | CH$_3$ | On-C$_4$H$_9$ | 4-CF$_3$-2-pyridyl | |
| 2.19 | N(CH$_3$)$_2$ | F | 5-C$_6$F$_{13}$-2-pyridyl | |
| 2.20 | CH$_3$ | Cl | 5-CF$_3$-2-pyridyl | |
| 2.21 | CH$_3$ | H | 6-CF$_3$-2-pyridyl | |
| 2.22 | CH$_3$ | OCF$_2$H | 3-CF$_3$-2-pyridyl | |
| 2.23 | i-Pr | Cl | 3-CH$_3$-2-pyridyl | |
| 2.24 | CH$_3$ | H | 3-CH$_3$-2-pyridyl | |
| 2.25 | n-C$_4$H$_9$ | n-C$_4$F$_9$ | 4-CH$_3$-2-pyridyl | |
| 2.26 | CH$_3$ | Cl | 4-CH$_3$-2-pyridyl | |
| 2.27 | CH$_3$ | Br | 5-CH$_3$-2-pyridyl | |
| 2.28 | CH$_3$ | H | 6-CH$_3$-2-pyridyl | |
| 2.29 | CH$_3$ | OC$_2$F$_5$ | 3-i-Pr-2-pyridyl | |
| 2.30 | CH$_3$ | N(n-C$_4$H$_9$)$_2$ | 4-n-Hex-2-pyridyl | |
| 2.31 | CH$_3$ | F | 5-Et-2-pyridyl | |
| 2.32 | CH$_3$ | H | 3-OCH$_2$-2-pyridyl | |
| 2.33 | CH$_3$ | Br | 4-OCH$_3$-2-pyridyl | |
| 2.34 | CH$_3$ | Cl | 5-OMe-2-pyridyl | |
| 2.35 | CH$_3$ | i-C$_3$H$_7$ | 6-OMe-2-pyridyl | |
| 2.36 | CH$_3$ | OC$_2$H$_5$ | 4-OEt$_2$-2-pyridyl | |
| 2.37 | CH$_3$ | N(CH$_3$(C$_2$H$_5$) | 4-Oi-Pr-2-pyridyl | |
| 2.38 | CH$_3$ | OCF$_3$ | 3-On-Hex-2-pyridyl | |
| 2.39 | N(CH$_3$)$_2$ | CF$_3$ | 5-Ot-Bu-2-pyridyl | |
| 2.40 | CH$_3$ | Cl | 3-OCF$_3$-2-pyridyl | |
| 2.41 | CH$_3$ | tert-C$_4$H$_9$ | 4-OCF$_3$-2-pyridyl | |
| 2.42 | CH$_3$ | H | 5-OCF$_3$-2-pyridyl | |
| 2.43 | CH$_3$ | H | 6-OCF$_3$-2-pyridyl | |
| 2.44 | CH$_3$ | Otert-C$_4$H$_9$ | 3-OCHF$_2$-2-pyridyl | |
| 2.45 | CH$_3$ | H | 4-OCHF$_2$-2-pyridyl | |
| 2.46 | CH$_3$ | Cl | 5-OCHF$_2$-2-pyridyl | |
| 2.47 | CH$_3$ | H | 6-OCHF$_2$-2-pyridyl | |
| 2.48 | CH$_3$ | I | 6-OCH$_2$CF$_3$-2-pyridyl | |
| 2.49 | CH$_3$ | C$_2$H$_5$ | C-OC$_6$F$_{13}$-2-pyridyl | |
| 2.50 | CH$_3$ | Oi-C$_3$H$_7$ | 6-NO$_2$-2-pyridyl | |
| 2.51 | CH$_3$ | On-C$_4$H$_9$ | 4-NO$_2$-2-pyridyl | |
| 2.52 | Et | Cl | 3-NO$_2$-2-pyridyl | |
| 2.53 | N(CH$_3$)$_2$ | H | 5-NO$_2$-2-pyridyl | |
| 2.54 | CH$_3$ | Br | 6-SMe-2-pyridyl | |
| 2.55 | CH$_3$ | Cl | 6-S-hexyl-2-pyridyl | |
| 2.56 | CH$_3$ | H | 4-SMe-2-pyridyl | |
| 2.57 | CH$_3$ | CH$_2$CF$_3$ | 6-SiPr-2-pyridyl | |
| 2.58 | CH$_3$ | Cl | 3-COOMe-2-pyridyl | |
| 2.59 | i-Pr | H | 5-COOBu-2-pyridyl | |
| 2.60 | CH$_3$ | CF$_3$ | 5-COOMe-2-pyridyl | |
| 2.61 | CH$_3$ | Cl | 6-COOi-Pr-2-pyridyl | |
| 2.62 | CH$_3$ | Oi-C$_3$H$_7$ | 5-CN-2-pyridyl | |
| 2.63 | CH$_3$ | Cl | 6-CN-2-pyridyl | |
| 2.64 | CH$_3$ | Br | 4-N(CH$_3$)$_2$-2-pyridyl | |
| 2.65 | CH$_3$ | OCF$_3$ | 3-N(Bu)$_2$-2-pyridyl | |
| 2.66 | CH$_3$ | H | 6-N(i-Pr)$_2$-2-pyridyl | |
| 2.67 | CH$_3$ | N(CH$_3$)$_2$ | 4-N(CH$_3$)(Et)-2-pyridyl | |
| 2.68 | CH$_3$ | H | 3,5-(Cl)$_2$-2-pyridyl | |
| 2.69 | CH$_3$ | H | 3-Cl,5-F-2-pyridyl | |
| 2.70 | CH$_3$ | OCH$_3$ | 3,4,5,6(Cl)$_4$-2-pyridyl | |
| 2.71 | CH$_3$ | CH$_3$ | 3-CF$_3$,5-Cl-2-pyridyl | |
| 2.72 | CH$_3$ | H | 3-Cl,5-CF$_3$-2-pyridyl | |

TABLE 2-continued

Structure: benzotriazole with $R_2$ and $R_4S$ substituents on benzene ring, $SO_2R_1$ on N-1; mixture of isomers

| Comp. No. | $R_1$ | $R_2$ | $R_4$ | m.p. |
|---|---|---|---|---|
| 2.73 | CH$_3$ | n-C$_4$H$_9$ | 6-Cl-3-CF$_3$-2-pyridyl | |
| 2.74 | CH$_3$ | CH$_3$ | 6-Cl-4-CF$_3$-2-pyridyl | |
| 2.75 | CH$_3$ | H | 6-Cl-5-CF$_3$-2-pyridyl | |
| 2.76 | n-Bu | OCF$_3$ | 6-Br-4-CF$_3$-2-pyridyl | |
| 2.77 | CH$_3$ | N(CH$_3$)$_2$ | 4-Cl,3-CH$_3$-2-pyridyl | |
| 2.78 | CH$_3$ | OCF$_3$ | 6-Cl-5-CH$_3$-2-pyridyl | |
| 2.79 | CH$_3$ | CH$_3$ | 4-Br-5-CH$_3$-2-pyridyl | |
| 2.80 | CH$_3$ | Cl | 6-CH$_3$-4-CF$_3$-2-pyridyl | |
| 2.81 | CH$_3$ | H | 3-CH$_3$-4-Br-2-pyridyl | |
| 2.82 | CH$_3$ | Cl | 4,6-(CH$_3$)$_2$-3-CN-2-pyridyl | 144–154° C. |
| 2.83 | CH$_3$ | Cl | 4-CH$_3$-3-pyridazinyl | |
| 2.84 | CH$_3$ | H | 2-Br-3-pyridyl | |
| 2.85 | CH$_3$ | Br | 2-Cl-3-pyridyl | |
| 2.86 | CH$_3$ | H | 2-I,6-CH$_3$-3-pyridyl | |
| 2.87 | CH$_3$ | OCH$_3$ | 5-Cl-3-pyridyl | |
| 2.88 | Et | Cl | 2,6(Br$_2$)-3-pyridyl | |
| 2.89 | CH$_3$ | H | 6(CH$_3$)-3-pyridyl | |
| 2.90 | CH$_3$ | Otert-C$_4$H$_9$ | 2-NO$_2$-3-pyridyl | |
| 2.91 | CH$_3$ | i-C$_3$H$_7$ | 2-NO$_2$-6-CH$_3$-3-pyridyl | |
| 2.92 | CH$_3$ | Cl | 2-[N(CH$_3$)$_2$]-3-pyridyl | |
| 2.93 | CH$_3$ | n-C$_4$F$_9$ | 2-COOMe-3-pyridyl | |
| 2.94 | CH$_3$ | Cl | 5-CF$_3$-3-pyridyl | |
| 2.95 | CH$_3$ | H | 2,3,5,6-(Cl$_4$)-4-pyridyl | |
| 2.96 | CH$_3$ | Cl | 3,5-Cl$_2$-4-pyridyl | |
| 2.97 | CH$_3$ | CH$_3$ | 2-CH$_3$-4-pyridyl | |
| 2.98 | CH$_3$ | Br | 2-COOMe-4-pyridyl | |
| 2.99 | CH$_3$ | Cl | 2-pyridyl | 158–161° C. |
| 2.100 | N(CH$_3$)$_2$ | F | 2-Cl-4-pyridyl | |
| 2.101 | CH$_3$ | H | 2-CF$_3$-4-pyridyl | |
| 2.102 | CH$_3$ | H | 2-pyrimidyl | |
| 2.103 | CH$_3$ | CF$_3$ | 4-pyrimidyl | |
| 2.104 | CH$_3$ | OCH$_3$ | 5-pyrimidyl | |
| 2.105 | CH$_3$ | Br | 4-CH$_3$-2-pyrimidyl | |
| 2.106 | CH$_3$ | Cl | 4,6-(CH$_3$)$_2$-2-pyrimidyl | 165–168.5° C. |
| 2.107 | N(CH$_3$)$_2$ | H | 4,6-(CH$_3$)$_2$-2-pyrimidyl | |
| 2.108 | CH$_3$ | Oi-C$_3$H$_7$ | 4-Cl-2-pyrimidyl | |
| 2.109 | CH$_3$ | Cl | 4,6(Cl)$_2$-2-pyrimidyl | |
| 2.110 | CH$_3$ | H | 4,5,6(Cl)$_3$-2-pyrimidyl | |
| 2.111 | CH$_3$ | CF$_3$ | 4-Cl-6-CH$_3$-2-pyrimidyl | |
| 2.112 | CH$_3$ | OCF$_3$ | 4-CF$_3$-5,6-F$_2$-2-pyrimidyl | |
| 2.113 | Et | Cl | 4-N(CH$_3$)$_2$-5-NO$_2$-6-CH$_3$-2-pyrimidyl | |
| 2.114 | CH$_3$ | OCF$_2$—CF$_2$H | 6(OCH$_3$)-2-pyrimidyl | |
| 2.115 | CH$_3$ | Cl | 4,6-F$_2$-2-pyrimidyl | |
| 2.116 | CH$_3$ | Br | 4-(CF$_3$)-5-COOMe-2-pyrimidyl | |
| 2.117 | Bu | N(CH$_3$)$_2$ | 4-N(Bu)$_2$-5-F-2-pyrimidyl | |
| 2.118 | CH$_3$ | H | 4-OC$_4$F$_9$-2-pyrimidyl | |
| 2.119 | CH$_3$ | Cl | 3-pyridazinyl | |
| 2.120 | CH$_3$ | H | 4,6-(OMe)$_2$-2-pyrimidyl | |
| 2.121 | CH$_3$ | H | 2,6-Cl$_2$-4-pyrimidyl | |
| 2.122 | CH$_3$ | Cl | 2-Cl,6-CH$_3$-4-pyrimidyl | |
| 2.123 | i-Pr | Br | 2-Cl-5-CH$_3$-4-pyrimidyl | |
| 2.124 | CH$_3$ | Cl | 5-Cl-6-Et-4-pyrimidyl | 176–183° C. |
| 2.125 | CH$_3$ | H | 2,6-(MeO)$_2$-4-pyrimidyl | |
| 2.126 | CH$_3$ | Cl | 2-Cl,5-F-4-pyrimidyl | |
| 2.127 | CH$_3$ | OCF$_3$ | 2,5-F$_2$-6-CF$_3$-4-pyrimidyl | |
| 2.128 | CH$_3$ | Cl | 2-Cl-6-N(CH$_3$)$_2$-4-pyrimidyl | |
| 2.129 | CH$_3$ | F | 2,6-F$_2$-4-pyrimidyl | |
| 2.130 | CH$_3$ | Cl | 2-SMe-6-Me-4-pyrimidyl | |
| 2.131 | CH$_3$ | H | 2-S-Pr-4-pyrimidyl | |
| 2.132 | CH$_3$ | Cl | 2-Cl-4-pyrimidyl | |
| 2.133 | CH$_3$ | OCH$_3$ | 2-SMe-6-Cl-4-pyrimidyl | |
| 2.134 | Bu | On-C$_3$H$_7$ | 2-CH$_3$,4-SMe,5-CN-4-pyrimidyl | |
| 2.135 | CH$_3$ | H | 2-CH$_2$-5-pyrimidyl | |
| 2.136 | CH$_3$ | Cl | 4-Cl-5-pyrimidyl | |
| 2.137 | CH$_3$ | CH$_3$ | 2-SBu-5-pyrimidyl | |
| 2.138 | CH$_3$ | OCF$_3$ | 2-CN-4-NO$_2$-5-pyrimidyl | |
| 2.139 | CH$_3$ | H | 2-MeO-5-pyrimidyl | |
| 2.140 | N(CH$_3$)$_2$ | H | 2-COOMe-5-pyrimidyl | |
| 2.141 | CH$_3$ | Cl | 4-N(Bu)$_2$-5-pyrimidyl | |
| 2.142 | CH$_3$ | N(n-C$_4$H$_9$)$_2$ | 2,4-Cl$_2$-5-pyrimidyl | |
| 2.143 | CH$_3$ | CF$_3$ | 2,4-(CH$_3$)$_2$-5-pyrimidyl | |

TABLE 2-continued

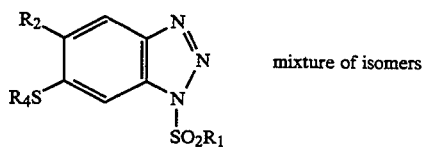

mixture of isomers

| Comp. No. | R₁ | R₂ | R₄ | m.p. |
|---|---|---|---|---|
| 2.144 | CH₃ | H | 2-pyrazinyl | |
| 2.145 | CH₃ | Cl | 3-chloro-2-pyrazinyl | 152–154° C. |
| 2.146 | CH₃ | Br | 6-chloro-2-pyrazinyl | |
| 2.147 | CH₃ | Cl | 3,6-Me₂-2-pyrazinyl | 131–133° C. |
| 2.148 | CH₃ | Cl | 3-Cl-5-N(Me)₂-6-COOMe-2-pyrazinyl | |
| 2.149 | N(CH₃)₂ | CH₃ | 3,5-(NBu₂)₂-6-CN-2-pyrazinyl | |
| 2.150 | Bu | OCH₃ | 3,5,6-(CH₃)₃-2-pyrazinyl | |
| 2.151 | CH₃ | H | 3-Et-2-pyrazinyl | |
| 2.152 | CH₃ | Cl | 5-OMe-2-pyrazinyl | |
| 2.153 | CH₃ | Br | 6-Br-2-pyrazinyl | |
| 2.154 | CH₃ | OCF₂H | 5-OMe-2-pyrazinyl | |
| 2.155 | CH₃ | Cl | 3-NO₂-2-pyrazinyl | |
| 2.156 | CH₃ | Br | 3,5(Cl)₂-2-pyridyl | |
| 2.157 | CH₃ | Cl | 3,5(Cl)₂-2-pyridyl | 141–143° C. |
| 2.158 | CH₃ | Cl | 3-F,5Cl-2-pyridyl | |
| 2.159 | CH₃ | Br | 3-Cl,5F-2-pyridyl | |
| 2.160 | CH₃ | F | 3-Cl,5(CF₃)-2-pyridyl | |
| 2.161 | CH₃ | Cl | 3-Cl,5(CF₃)-2-pyridyl | 167–168° C. |
| 2.162 | CH₃ | Br | 3-Cl,5(CF₃)-2-pyridyl | |
| 2.163 | CH₃ | Cl | 4,6(OCH₃)₂-2-pyrimidyl | |
| 2.164 | CH₃ | Br | 4,6(OCH₃)₂-2-pyrimidyl | |
| 2.165 | CH₃ | Cl | 6-Cl-2-pyrazinyl | 147–149° C. |
| 2.166 | CH₃ | Cl | 6-OCH₃-3-pyradazinyl | 176–179° C. |
| 2.167 | CH₃ | Cl | 6-CH₃-3-pyridazinyl | 174–177° C. |
| 2.168 | CH₃ | Cl | 6-Cl-3-pyridazinyl | 187–190° C. |
| 2.169 | CH₃ | H | 4-CH₃-2-pyrimidyl | 103–106° C. |
| 2.170 | CH₃ | Br | 4,6-(CH₃)₂-2-pyrimidyl | 152–154° C. |
| 2.171 | CH₃ | Cl | 5-Cl-6-(n-C₃H₇)-4-pyrimidyl | 164–165° C. |
| 2.172 | CH₃ | Cl | 5-Cl-6-CH₃-4-pyrimidyl | 175–176° C. |
| 2.173 | CH₃ | Cl | 2-SCH₃-5-OCH₃-4-pyrimidyl | 165–170° C. |
| 2.174 | CH₃ | Cl | 2,6-(OCH₃)₂-4-pyrimidyl | 179–181° C. |
| 2.175 | CH₃ | Cl | 2,6-Cl₂-4-pyrimidyl | 219–225° C. |
| 2.176 | CH₃ | Cl | 2-pyrimidyl | 130–134° C. |
| 2.177 | CH₃ | H | 5-CF₃-2-pyridyl | 107–109° C. |

TABLE 3

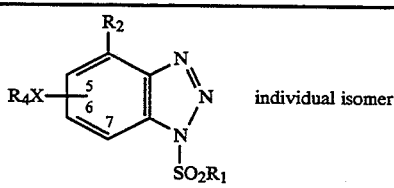

individual isomer

| Comp. No. | R₁ | R₂ | R₄ | X | m.p. |
|---|---|---|---|---|---|
| 3.1 | CH₃ | H | 2-pyridyl | 5-S | |
| 3.2 | Et | Cl | 2-pyridyl | 6-O | |
| 3.3 | i-Pr | F | 2-pyridyl | 6-S | |
| 3.4 | N(CH₃)₂ | Br | 2-pyridyl | 5-O | |
| 3.5 | CH₃ | CH₃ | 3-pyridyl | 6-O | |
| 3.6 | CH₃ | Cl | 4-pyridyl | 6-S | |
| 3.7 | CH₃ | CH₃O | 3-Cl-2-pyridyl | 5-S | |
| 3.8 | i-Pr | CF₃ | 3-Cl-2-pyridyl | 6-O | |
| 3.9 | CH₃ | OCF₃ | 4-Cl-2-pyridyl | 6-S | |
| 3.10 | CH₃ | Cl | 4-Cl-2-pyridyl | 6-O | |
| 3.11 | N(CH₃)₂ | Br | 5-Cl-2-pyridyl | 5-S | |
| 3.12 | CH₃ | I | 5-Cl-2-pyridyl | 6-S | |
| 3.13 | CH₃ | C₂H₅ | 6-Cl-2-pyridyl | 6-O | |
| 3.14 | Bu | Br | 4-Br-2-pyridyl | 6-O | |
| 3.15 | CH₃ | Cl | 4-Br-2-pyridyl | 5-S | |
| 3.16 | CH₃ | Cl | 3-F-2-pyridyl | 6-S | |
| 3.17 | CH₃ | Br | 3-CF₃-2-pyridyl | 5-O | |
| 3.18 | CH₃ | On-C₄H₉ | 4-CF₃-2-pyridyl | 5-O | |
| 3.19 | N(CH₃)₂ | Br | 5-CF₃-2-pyridyl | 6-O | |
| 3.20 | CH₃ | Cl | 5-CF₃-2-pyridyl | 6-O | 157–159° C. |

TABLE 3-continued

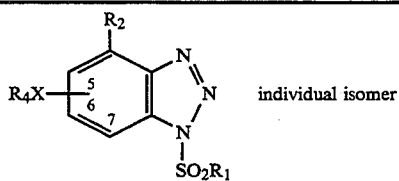

individual isomer

| Comp. No. | $R_1$ | $R_2$ | $R_4$ | X | m.p. |
|---|---|---|---|---|---|
| 3.21 | $CH_3$ | Br | 6-$CF_3$-2-pyridyl | 5-S | |
| 3.22 | $CH_3$ | $OCH_3$ | 3-$C_6F_{13}$-2-pyridyl | 6-O | |
| 3.23 | $CH_3$ | $OC_2F_5$ | 3-$CH_3$-2-pyridyl | 6-S | |
| 3.24 | $CH_3$ | Cl | 3-$CH_3$-2-pyridyl | 5-S | |
| 3.25 | $N(CH_3)_2$ | n-$C_4F_9$ | 4-$CH_3$-2-pyridyl | 5-S | |
| 3.26 | $CH_3$ | Cl | 4-$CH_3$-2-pyridyl | 6-O | |
| 3.27 | $CH_3$ | Br | 5-$CH_3$-2-pyridyl | 6-S | |
| 3.28 | $CH_3$ | Br | 6-$CH_3$-2-pyridyl | 5-O | |
| 3.29 | $CH_3$ | On-$C_4H_9$ | 3-i-Pr-2-pyridyl | 6-S | |
| 3.30 | $CH_3$ | $N(n-C_4H_9)_2$ | 4-n-Hex-2-pyridyl | 6-S | |
| 3.31 | $CH_3$ | F | 5-Et-2-pyridyl | 5-S | |
| 3.32 | $CH_3$ | Br | 3-$OCH_2$-2-pyridyl | 5-O | |
| 3.33 | $CH_3$ | Br | 4-$OCH_3$-2-pyridyl | 6-S | |
| 3.34 | $CH_3$ | Cl | 5-OMe-2-pyridyl | 6-O | |
| 3.35 | $CH_3$ | i-$C_3H_7$ | 6-OMe-2-pyridyl | 6-O | |
| 3.36 | $CH_3$ | $OC_2H_5$ | 4-OEt$_2$-2-pyridyl | 6-O | |
| 3.37 | $CH_3$ | $N(CH_3(C_2H_5))$ | 4-Oi-Pr-2-pyridyl | 5-S | |
| 3.38 | $CH_3$ | Br | 3-On-Hex-2-pyridyl | 6-S | |
| 3.39 | $N(CH_3)_2$ | $CF_3$ | 5-Ot-Bu-2-pyridyl | 5-S | |
| 3.40 | $CH_3$ | Cl | 3-$OCF_3$-2-pyridyl | 6-O | |
| 3.41 | $CH_3$ | tert-$C_4H_9$ | 4-$OCF_3$-2-pyridyl | 6-S | |
| 3.42 | $CH_3$ | Br | 5-$OCF_3$-2-pyridyl | 5-S | |
| 3.43 | $CH_3$ | Br | 6-$OCF_3$-2-pyridyl | 5-O | |
| 3.44 | $CH_3$ | Otert-$C_4H_9$ | 3-$OCHF_2$-2-pyridyl | 6-O | |
| 3.45 | $CH_3$ | Br | 4-$OCHF_2$-2-pyridyl | 5-S | |
| 3.46 | $CH_3$ | Cl | 5-$OCHF_2$-2-pyridyl | 6-S | |
| 3.47 | $CH_3$ | Br | 6-$OCHF_2$-2-pyridyl | 5-O | |
| 3.48 | $N(CH_3)_2$ | Br | 6-$OCH_2CF_3$-2-pyridyl | 6-O | |
| 3.49 | $CH_3$ | Br | 6-$OC_6F_{13}$-2-pyridyl | 6-S | |
| 3.50 | $CH_3$ | Oi-$C_3H_7$ | 6-$NO_2$-2-pyridyl | 5-S | |
| 3.51 | $CH_3$ | On-$C_4H_9$ | 4-$NO_2$-2-pyridyl | 6-O | |
| 3.52 | Et | Cl | 3-$NO_2$-2-pyridyl | 6-S | |
| 3.53 | $N(CH_3)_2$ | Br | 5-$NO_2$-2-pyridyl | 5-S | |
| 3.54 | $CH_3$ | Br | 6-SMe-2-pyridyl | 6-O | |
| 3.55 | $CH_3$ | $OCF_3$ | 6-S-hexyl-2-pyridyl | 5-S | |
| 3.56 | $CH_3$ | $OCH_3$ | 4-SMe-2-pyridyl | 5-O | |
| 3.57 | $CH_3$ | $CH_2CF_3$ | 5-Cl-2-pyridyl | 6-O | |
| 3.58 | $CH_3$ | Cl | 3-COOMe-2-pyridyl | 6-S | |
| 3.59 | i-Pr | $N(CH_3)_2$ | 5-COOBu-2-pyridyl | 5-S | |
| 3.60 | $CH_3$ | $CF_3$ | 5-COOMe-2-pyridyl | 6-O | |
| 3.61 | $CH_3$ | Cl | 6-COOi-Pr-2-pyridyl | 5-O | |
| 3.62 | $CH_3$ | Br | 5-$CH_3$-2-pyridyl | 6-S | |
| 3.63 | $CH_3$ | Cl | 6-CN-2-pyridyl | 6-O | |
| 3.64 | $CH_3$ | Br | 4-$N(CH_3)_2$-2-pyridyl | 5-S | |
| 3.65 | $CH_3$ | $OC_2H_5$ | 3-$N(Bu)_2$-2-pyridyl | 6-S | |
| 3.66 | $CH_3$ | $CF_3$ | 6-$N(i-Pr)_2$-2-pyridyl | 5-O | |
| 3.67 | $CH_3$ | Br | 4-$N(CH_3)(Et)$-2-pyridyl | 6-O | |
| 3.68 | $CH_3$ | Br | 3,5-$(Cl)_2$-2-pyridyl | 5-O | |
| 3.69 | $CH_3$ | Br | 3-Cl,5-F-2-pyridyl | 5-S | |
| 3.70 | $CH_3$ | $OCH_3$ | 3,4,5,6$(Cl)_4$-2-pyridyl | 6-O | |
| 3.71 | $CH_3$ | $CH_3$ | 3-$CF_3$, 5-Cl-2-pyridyl | 6-O | |
| 3.72 | $CH_3$ | Br | 3-Cl,5-$CF_3$-2-pyridyl | 5-S | |
| 3.73 | $CH_3$ | $OCH_3$ | 6-Cl-3-$CF_3$-2-pyridyl | 6-S | |
| 3.74 | $CH_3$ | $CH_3$ | 6-Cl-4-$CF_3$-2-pyridyl | 5-S | |
| 3.75 | $CH_3$ | $OCH_3$ | 6-Cl-5-$CF_3$-2-pyridyl | 5-O | |
| 3.76 | n-Bu | Br | 6-Br-4-$CF_3$-2-pyridyl | 6-O | |
| 3.77 | $CH_3$ | $N(CH_3)_2$ | 4-Cl,3-$CH_3$-2-pyridyl | 6-S | |
| 3.78 | $CH_3$ | $OCF_3$ | 6-Cl-5-$CH_3$-2-pyridyl | 5-S | |
| 3.79 | $CH_3$ | $CH_3$ | 4-Br-5-$CH_3$-2-pyridyl | 6-O | |
| 3.80 | $CH_3$ | Cl | 6-$CH_3$-4-$CF_3$-2-pyridyl | 5-O | |
| 3.81 | $N(CH_3)_2$ | $C_2H_5$ | 3-$CH_3$-4-Br-2-pyridyl | 5-S | |
| 3.82 | $CH_3$ | Cl | 4,6-$(CH_3)_2$-3-CN-2-pyridyl | 6-O | |
| 3.83 | $CH_3$ | Br | 3-pyridazinyl | 6-S | |
| 3.84 | $CH_3$ | Br | 2-Br-3-pyridyl | 5-S | |
| 3.85 | $CH_3$ | Br | 2-Cl-3-pyridyl | 6-O | |
| 3.86 | $CH_3$ | Cl | 2-I,6-$CH_3$-3-pyridyl | 6-S | |
| 3.87 | $CH_3$ | $OCH_3$ | 5-Cl-3-pyridyl | 5-S | |
| 3.88 | Et | Cl | 2,6-$(Br_2)$-3-pyridyl | 6-O | |
| 3.89 | $CH_3$ | Br | 6$(CH_3)$-3-pyridyl | 5-O | |
| 3.90 | $CH_3$ | Br | 2-$NO_2$-3-pyridyl | 6-O | |
| 3.91 | $CH_3$ | i-$C_3H_7$ | 2-$NO_2$-6-$CH_3$-3-pyridyl | 5-S | |

TABLE 3-continued

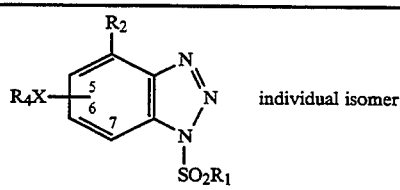

individual isomer

| Comp. No. | R₁ | R₂ | R₄ | X | m.p. |
|---|---|---|---|---|---|
| 3.92 | CH₃ | Br | 2-[N(CH₃)₂]-3-pyridyl | 5-O | |
| 3.93 | CH₃ | n-C₄F₉ | 2-COOMe-3-pyridyl | 6-S | |
| 3.94 | N(CH₃)₂ | Cl | 5-CF₃-3-pyridyl | 5-S | |
| 3.95 | CH₃ | Br | 2,3,4,6-(Cl₄)-4-pyridyl | 5-O | |
| 3.96 | CH₃ | Cl | 3,5-Cl₂-4-pyridyl | 6-S | |
| 3.97 | CH₃ | CH₃ | 2-CH₃-4-pyridyl | 6-S | |
| 3.98 | CH₃ | Br | 2-COOMe-4-pyridyl | 6-O | |
| 3.99 | Et | Br | 2-Br-4-pyridyl | 5-O | |
| 3.100 | N(CH₃)₂ | F | 2-Cl-4-pyridyl | 6-S | |
| 3.101 | CH₃ | Br | 2-CF₃-4-pyridyl | 5-S | |
| 3.102 | CH₃ | CH₃ | 2-pyrimidyl | 5-O | |
| 3.103 | CH₃ | CF₃ | 4-pyrimidyl | 5-S | |
| 3.104 | CH₃ | OCH₃ | 5-pyrimidyl | 6-O | |
| 3.105 | CH₃ | Br | 4-CH₃-2-pyrimidyl | 6-S | |
| 3.106 | CH₃ | Cl | 4,6-(CH₃)₂-2-pyrimidyl | 6-S | |
| 3.107 | N(CH₃)₂ | OCF₃ | 4,6-(CH₃)₂-2-pyrimidyl | 5-S | |
| 3.108 | CH₃ | Oi-C₃H₇ | 4-Cl-2-pyrimidyl | 6-O | |
| 3.109 | CH₃ | Cl | 4,6(Cl)₂-2-pyrimidyl | 5-S | |
| 3.110 | CH₃ | C₂H₅ | 4,5,6(Cl)₃-2-pyrimidyl | 5-O | |
| 3.111 | CH₃ | Br | 4-Cl-6-CH₃-2-pyrimidyl | 6-O | |
| 3.112 | CH₃ | OCF₃ | 4-CF₃-5,6-F₂-2-pyrimidyl | 5-S | |
| 3.113 | CH₃ | Cl | 4-CH₃-3-pyridazinyl | 6-O | |
| 3.114 | CH₃ | Br | 4-(CH₃)-6-(OCH₃)-2-pyrimidyl | 6-O | |
| 3.115 | CH₃ | Cl | 4,6-F₂-2-pyrimidyl | 6-O | |
| 3.116 | CH₃ | Br | 4-(CF₃)-5-COOMe-2-pyrimidyl | 6-O | |
| 3.117 | Bu | N(CH₃)₂ | 4-N(Bu)₂-5-F-2-pyrimidyl | 5-S | |
| 3.118 | CH₃ | Br | 4-OC₄F₉-2-pyrimidyl | 5-S | |
| 3.119 | N(CH₃)₂ | Cl | 4-(Cl)-5-(CH₃)-2-pyrimidyl | 6-S | |
| 3.120 | CH₃ | Br | 4,6-(OMe)₂-2-pyrimidyl | 5-O | |
| 3.121 | CH₃ | Cl | 2,6-Cl₂-1-pyrimidyl | 5-O | |
| 3.122 | CH₃ | OCF₂—CF₂H | 2-Cl,6-CH₃-4-pyrimidyl | 6-O | |
| 3.123 | i-Pr | Br | 2-Cl-5-CH₃-4-pyrimidyl | 6-S | |
| 3.124 | CH₃ | Cl | 5-Cl-6-Et-4-pyrimidyl | 6-S | |
| 3.125 | CH₃ | Br | 2,6-(MeO)₂-4-pyrimidyl | 5-S | |
| 3.126 | Bu | Cl | 2-Cl,5-F-4-pyrimidyl | 6-O | |
| 3.127 | CH₃ | OCF₃ | 2,5-F₂-6-CF₃-4-pyrimidyl | 6-O | |
| 3.128 | CH₃ | Cl | 2-Cl-6-N(CH₃)₂-4-pyrimidyl | 5-S | |
| 3.129 | CH₃ | F | 2,6-F₂-4-pyrimidyl | 5-O | |
| 3.130 | CH₃ | Cl | 2-SMe-6-Me-4-pyrimidyl | 6-O | |
| 3.131 | CH₃ | Br | 2-S-Pr-4-pyrimidyl | 5-O | |
| 3.132 | CH₃ | Cl | 2-Cl-4-pyrimidyl | 6-S | |
| 3.133 | CH₃ | I | 2-SMe-6-Cl-4-pyrimidyl | 5-O | |
| 3.134 | CH₃ | Cl | 5-MeO-3-pyridazinyl | 6-O | |
| 3.135 | CH₃ | Br | 2-CH₂-5-pyrimidyl | 5-O | |
| 3.136 | CH₃ | Cl | 4-Cl-5-pyrimidyl | 6-S | |
| 3.137 | CH₃ | CH₃ | 2-SBu-5-pyrimidyl | 6-O | |
| 3.138 | CH₃ | Br | 2-CN-4-NO₂-5-pyrimidyl | 6-O | |
| 3.139 | CH₃ | N(n-C₄H₉)₂ | 2-MeO-5-pyrimidyl | 5-S | |
| 3.140 | N(CH₃)₂ | Br | 2-COOMe-5-pyrimidyl | 5-S | |
| 3.141 | CH₃ | Cl | 4-N(Bu)₂-5-pyrimidyl | 5-O | |
| 3.142 | CH₃ | Cl | 2,4-Cl₂-5-pyrimidyl | 6-O | |
| 3.143 | CH₃ | CF₃ | 2,4-(CH₃)₂-5-pyrimidyl | 5-S | |
| 3.144 | CH₃ | Br | 2-pyrazinyl | 5-O | |
| 3.145 | CH₃ | Cl | 3-chloro-2-pyrazinyl | 6-O | |
| 3.146 | CH₃ | OCF₃ | 6-chloro-2-pyrazinyl | 5-S | |
| 3.147 | CH₃ | Cl | 3,6-Me₂-2-pyrazinyl | 6-S | |
| 3.148 | CH₃ | Br | 6-COOMe-2-pyrazinyl | 6-O | |
| 3.149 | N(CH₃)₂ | CH₃ | 3,5-(NBu₂)₂-6-CN-2-pyrazinyl | 5-S | |
| 3.150 | Bu | OCH₃ | 3,5,6-(CH₃)₃-2-pyrazinyl | 5-O | |
| 3.151 | CH₃ | Cl | 3-Et-2-pyrazinyl | 6-O | |
| 3.152 | N(Et)₂ | Cl | 5-OMe-2-pyrazinyl | 6-S | |
| 3.153 | CH₃ | Br | 6-Br-2-pyrazinyl | 5-O | |
| 3.154 | CH₃ | Br | 5-OMe-2-pyrazinyl | 5-S | |
| 3.155 | CH₃ | Cl | 3-NO₂-2-pyrazinyl | 6-S | |
| 3.156 | CH₃ | OCF₂H | 3,5(Cl)₂-2-pyridyl | 6-O | |
| 3.157 | CH₃ | Cl | 3,5(Cl)₂-2-pyridyl | 5-S | |
| 3.158 | CH₃ | Cl | 3-Cl,5F-2-pyridyl | 6-O | |
| 3.159 | CH₃ | Br | 3-Cl,5F-2-pyridyl | 6-S | |
| 3.160 | CH₃ | F | 3-Cl,5(CF₃)-2-pyridyl | 5-S | |
| 3.161 | CH₃ | Cl | 3-Cl,5(CF₃)-2-pyridyl | 5-O | |
| 3.162 | CH₃ | Br | 3-Cl,5(CF₃)-2-pyridyl | 6-) | 159–160° C. |

TABLE 3-continued

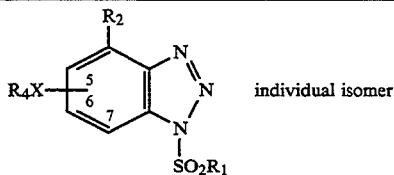

individual isomer

| Comp. No. | $R_1$ | $R_2$ | $R_4$ | X | m.p. |
|---|---|---|---|---|---|
| 3.163 | $CH_3$ | Cl | 4,6$(OCH_3)_2$-2-pyrimidyl | 6-O | |
| 3.164 | $CH_3$ | Br | 4,6$(OCH_3)_2$-2-pyrimidyl | 6-S | |
| 3.165 | $CH_3$ | Br | 5-Cl-6-Et-4-pyrimidyl | 6-O | 164–165° C. |
| 3.166 | $CH_3$ | Cl | 3-Cl-5-$CF_3$-2-pyridyl | 6-O | 157–160° C. |
| 3.167 | $N(CH_3)_2$ | Cl | 5-$CF_3$-2-pyridyl | 6-O | 153–155° C. |
| 3.168 | $N(CH_3)_2$ | Cl | 3-Cl-5-$CF_3$-2-pyridyl | 6-O | 137–143° C. |
| 3.169 | $CH_3$ | Br | 3-F-5-Cl-2-pyridyl | 6-O | 178–179° C. |
| 3.170 | $N(CH_3)_2$ | Br | 3-F-5-Cl-2-pyridyl | 6-O | 148–149° C. |
| 3.171 | $CH_3$ | Br | 6-$OCH_3$-3-pyridazinyl | 6-O | 187–188° C. |
| 3.172 | $CH_3$ | Br | 5-COOEt-2-pyridyl | 6-O | 199–201° C. |
| 3.173 | $CH_3$ | Br | 3-$CH_3$-2-pyrimidyl | 6-O | 192–193° C. |
| 3.174 | $N(CH_3)_2$ | Br | 3-$CH_3$-2-pyrimidyl | 6-O | 179–181° C. |
| 3.175 | $CH_3$ | Br | 2,6-$(OCH_3)_2$-4-pyrimidyl | 6-O | |
| 3.176 | $CH_3$ | Br | 3-ethyl-2-pyrazinyl | 6-O | |
| 3.177 | $CH_3$ | Br | 6-$CH_3$-3-pyridazinyl | 6-O | |
| 3.178 | $CH_3$ | Br | 6-$OCH_3$-3-pyridazinyl | 6-O | 187–188° C. |
| 3.179 | $CH_3$ | Br | 6-Cl-3-pyridazinyl | 6-O | |
| 3.180 | $CH_3$ | Br | 4,5-$Cl_2$-3-pyridazinyl | 6-O | |
| 3.181 | $N(CH_3)_2$ | Br | 5-Cl-6-$CH_3$-4-Pyrimidyl | 6-O | 166–169° C. |
| 3.182 | $CH_3$ | Br | 5-Cl-6-$CH_3$-4-Pyrimidyl | 6-O | 188–190° C. |

TABLE 4

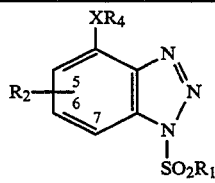

| Comp. No. | $R_1$ | $R_2$ | $R_4$ | X | m.p. |
|---|---|---|---|---|---|
| 4.1 | $CH_3$ | 5-H | 2-pyridyl | S | |
| 4.2 | Et | 5-Cl | 2-pyridyl | O | |
| 4.3 | s-$C_4H_9$ | 6-Br | 2-pyridyl | O | |
| 4.4 | $N(CH_3)_2$ | 5-F | 2-pyridyl | O | |
| 4.5 | $CH_3$ | 6-$CH_3$ | 3-pyridyl | S | |
| 4.6 | $CH_3$ | 6-Cl | 4-pyridyl | S | |
| 4.7 | $CH_3$ | 5-$CH_3O$ | 3-Cl-2-pyridyl | S | |
| 4.8 | $CH_3$ | 6-$CF_3$ | 3-Cl-2-pyridyl | O | |
| 4.9 | $CF_3$ | 5-Cl | 4-Cl-2-pyridyl | S | |
| 4.10 | $CH_3$ | 6-Cl | 4-Cl-2-pyridyl | S | |
| 4.11 | $N(CH_3)_2$ | 5-H | 5-Cl-2-pyridyl | O | |
| 4.12 | $CH_3$ | 6-Br | 5-Cl-2-pyridyl | O | |
| 4.13 | $CH_3$ | 6-$C_2H_5$ | 6-Cl-2-pyridyl | S | |
| 4.14 | $CH_3$ | 5-n-$C_4H_9$ | 4-Br-2-pyridyl | O | |
| 4.15 | $CH_3$ | 6-$N(CH_3)_2$ | 4-Br-2-pyridyl | O | |
| 4.16 | $N(CH_3)_2$ | 6-Cl | 3-F-2-pyridyl | O | |
| 4.17 | $CH_3$ | 6-Br | 3-$CF_3$-2-pyridyl | S | |
| 4.18 | $CH_3$ | 5-On-$C_4H_9$ | 4-$CF_3$-2-pyridyl | O | |
| 4.19 | $N(CH_3)_2$ | 6-F | 5-$CF_3$-2-pyridyl | S | |
| 4.20 | $CH_3$ | 5-Cl | 5-$CF_3$-2-pyridyl | S | |
| 4.21 | $CH_3$ | 5-H | 6-$CF_3$-2-pyridyl | S | |
| 4.22 | $CH_3$ | 5-$OCF_2H$ | 3-$CH_3$-2-pyridyl | O | |
| 4.23 | i-Pr | 6-Br | 3-$CH_3$-2-pyridyl | S | |
| 4.24 | $CH_3$ | 5-H | 3-$CH_3$-2-pyridyl | O | |
| 4.25 | $CH_3$ | 6-n-$C_4H_9$ | 4-$CH_3$-2-pyridyl | S | |
| 4.26 | $CH_3$ | 6-Cl | 4-$CH_3$-2-pyridyl | O | |
| 4.27 | n-$C_4H_9$ | 6-Br | 5-$CH_3$-2-pyridyl | O | |
| 4.28 | $CH_3$ | 6-H | 6-$CH_3$-2-pyridyl | S | |
| 4.29 | $CH_3$ | 6-On-$C_4H_9$ | 3-i-Pr-2-pyridyl | O | |
| 4.30 | $CH_3$ | 6-N(n-$C_4H_9$)$_2$ | 4-n-Hex-2-pyridyl | S | |
| 4.31 | $CH_3$ | 5-F | 5-Et-2-pyridyl | O | |
| 4.32 | $N(CH_3)_2$ | 6-H | 3-$OCH_2$-2-pyridyl | O | |
| 4.33 | $CH_3$ | 5-Br | 4-$OCH_2$-3-pyridyl | O | |
| 4.34 | $CH_3$ | 5-Cl | 5-OMe-2-pyridyl | O | |
| 4.35 | $CH_3$ | 6-i-$C_3H_7$ | 6-OMe-2-pyridyl | O | |

TABLE 4-continued

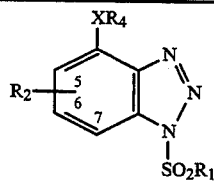

| Comp. No. | R₁ | R₂ | R₄ | X | m.p. |
|---|---|---|---|---|---|
| 4.36 | CH₃ | 6-OC₂H₅ | 4-OEt₂-2-pyridyl | S | |
| 4.37 | CH₃ | 6-Br | 4-Oi-Pr-2-pyridyl | O | |
| 4.38 | CH₃ | 5-OCF₃ | 3-On-Hex-2-pyridyl | S | |
| 4.39 | CH₃ | 5-CF₃ | 5-Ot-Bu-2-pyridyl | S | |
| 4.40 | CH₃ | 6-Cl | 3-OCF₃-2-pyridyl | O | |
| 4.41 | CH₃ | 6-Et | 4-OCF₃-2-pyridyl | O | |
| 4.42 | CH₃ | 5-H | 5-OCF₃-2-pyridyl | O | |
| 4.43 | CH₃ | 6-H | 6-OCF₃-2-pyridyl | O | |
| 4.44 | CH₃ | 6-Otert-C₄H₉ | 3-OCHF₂-2-pyridyl | S | |
| 4.45 | CH₃ | 6-H | 4-OCHF₂-2-pyridyl | S | |
| 4.46 | N(CH₃)₂ | 6-Cl | 5-OCHF₂-2-pyridyl | O | |
| 4.47 | CH₃ | 5-H | 6-OCHF₂-2-pyridyl | O | |
| 4.48 | CH₃ | 6-Br | 6-OCH₂CF₃-2-pyridyl | S | |
| 4.49 | CH₃ | 6-C₂H₅ | 6-OC₆F₁₃-2-pyridyl | S | |
| 4.50 | CH₃ | 5-Oi-C₃H₇ | 6-NO₂-2-pyridyl | O | |
| 4.51 | CH₃ | 6-Br | 4-NO₂-2-pyridyl | O | |
| 4.52 | Et | 5-Cl | 3-NO₂-2-pyridyl | O | |
| 4.53 | N(CH₃)₂ | 5-H | 5-NO₂-2-pyridyl | O | |
| 4.54 | CH₃ | 6-Br | 6-SMe-2-pyridyl | S | |
| 4.55 | CH₃ | 5-Br | 6-S-hexyl-2-pyridyl | O | |
| 4.56 | CH₃ | 5-H | 4-SMe-2-pyridyl | S | |
| 4.57 | CH₃ | 6-CF₃ | 6-Si-Pr-2-pyridyl | O | |
| 4.58 | CH₃ | 6-Cl | 3-COOMe-2-pyridyl | O | |
| 4.59 | i-Pr | 5-H | 5-COOBu-2-pyridyl | S | |
| 4.60 | CH₃ | 6-CF₃ | 5-COOMe-2-pyridyl | S | |
| 4.61 | CH₃ | 6-Cl | 6-COOi-Pr-2-pyridyl | O | |
| 4.62 | CH₃ | 6-Oi-C₃H₇ | 5-CN-2-pyridyl | S | |
| 4.63 | CH₃ | 6-Cl | 6-CN-2-pyridyl | O | |
| 4.64 | CH₃ | 5-Br | 4-N(CH₃)₂-2-pyridyl | S | |
| 4.65 | CH₃ | 6-OCF₃ | 3-N(Bu)₂-2-pyridyl | S | |
| 4.66 | CH₃ | 5-H | 6-N(i-Pr)₂-2-pyridyl | O | |
| 4.67 | CH₃ | 6-N(CH₃)₂ | 4-N(CH₃)(Et)-2-pyridyl | S | |
| 4.68 | CH₃ | 5-H | 3,5-(Cl)₂-2-pyridyl | O | |
| 4.69 | CH₃ | 5-H | 3-Cl,5-F-2-pyridyl | O | |
| 4.70 | CH₃ | 6-OCH₃ | 3,4,5,6(Cl)₄-2-pyridyl | S | |
| 4.71 | CH₃ | 5-CH₃ | 3-CF₃,5-Br-2-pyridyl | O | |
| 4.72 | CH₃ | 5-H | 3-Cl,5-CF₃-2-pyridyl | O | |
| 4.73 | CH₃ | 6-Oi-C₃H₇ | 6-Cl-3-CF₃-2-pyridyl | S | |
| 4.74 | CH₃ | 6-Cl | 6-Cl-4-CF₃-2-pyridyl | S | |
| 4.75 | CH₃ | 5-H | 6-Cl-4-CF₃-2-pyridyl | S | |
| 4.76 | n-Bu | 6-Br | 6-Br-4-CF₃-2-pyridyl | S | |
| 4.77 | CH₃ | 5-N(CH₃)₂ | 4-Cl,3-CH₃-2-pyridyl | S | |
| 4.78 | N(CH₃)₂ | 5-OCF₃ | 6-Cl-5-CH₃-2-pyridyl | O | |
| 4.79 | CH₃ | 6-CH₃ | 4-Br-5-CH₃-2-pyridyl | S | |
| 4.80 | CH₃ | 6-Cl | 6-CH₃-4-CF₃-2-pyridyl | S | |
| 4.81 | CH₃ | 5-H | 3-CH₃-4-Br-2-pyridyl | S | |
| 4.82 | CH₃ | 6-Cl | 4,6-(CH₃)₂-3-CN-2-pyridyl | S | |
| 4.83 | Et | 5-Cl | 3-COOMe-2-pyridyl | O | |
| 4.84 | CH₃ | 5-H | 2-Br-3-pyridyl | O | |
| 4.85 | CH₃ | 6-Br | 2-Cl-3-pyridyl | O | |
| 4.86 | CH₃ | 6-n-C₄H₉ | 2-Cl,6-CH₃-3-pyridyl | S | |
| 4.87 | CH₃ | 5-OCH₃ | 5-Cl-3-pyridyl | O | |
| 4.88 | CH₃ | 6-Cl | 2,6-(Br₂)-3-pyridyl | S | |
| 4.89 | CH₃ | 5-H | 6(CH₃)-3-pyridyl | O | |
| 4.90 | CH₃ | 5-Cl | 2-NO₂-3-pyridyl | S | |
| 4.91 | CH₃ | 5-i-C₃H₇ | 2-NO₂-6-CH₃-3-pyridyl | S | |
| 4.92 | CH₃ | 6-Cl | 2-[N(CH₃)₂]-3-pyridyl | O | |
| 4.93 | CH₃ | 6-n-C₄F₉ | 2-COOMe-3-pyridyl | S | |
| 4.94 | CH₃ | 6-Cl | 5-CF₃-3-pyridyl | S | |
| 4.95 | CH₃ | 5-Br | 2,3,5,6-(Cl)₄-4-pyridyl | O | |
| 4.96 | N(CH₃)₂ | 6-Cl | 3,5-Cl₂-4-pyridyl | S | |
| 4.97 | CH₃ | 5-CH₃ | 2-CH₃-4-pyridyl | O | |
| 4.98 | CH₃ | 6-Br | 2-COOMe-4-pyrdyl | S | |
| 4.99 | Et | 6-sec-C₄H₉ | 2-Br-4-pyridyl | S | |
| 4.100 | N(CH₃)₂ | 5-F | 2-Cl-4-pyridyl | O | |
| 4.101 | CH₃ | 5-H | 2-CF₃-4-pyridyl | O | |
| 4.102 | CH₃ | 5-H | 2-pyrimidyl | O | |
| 4.103 | CH₃ | 6-CF₃ | 4-pyrimidyl | O | |
| 4.104 | CH₃ | 5-OCH₃ | 5-pyrimidyl | O | |
| 4.105 | CH₃ | 5-Br | 4-CH₃-2-pyrimidyl | S | |
| 4.106 | CH₃ | 6-Cl | 4,6-(CH₃)₂-2-pyrimidyl | O | |

TABLE 4-continued

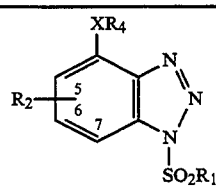

| Comp. No. | $R_1$ | $R_2$ | $R_4$ | X | m.p. |
|---|---|---|---|---|---|
| 4.107 | $N(CH_3)_2$ | 5-H | 4,6-$(CH_3)_2$-2-pyrimidyl | S | |
| 4.108 | $CH_3$ | 6-Oi-$C_3H_7$ | 4-Cl-2-pyrimidyl | O | |
| 4.109 | $CH_3$ | 6-Cl | 4,6-$(Cl)_2$-2-pyrimidyl | O | |
| 4.110 | $CH_3$ | 5-H | 4,5,6-$(Cl)_3$-2-pyrimidyl | O | |
| 4.111 | $CH_3$ | 6-$CF_3$ | 4-Cl-6-$CH_3$-2-pyrimidyl | S | |
| 4.112 | $CH_3$ | 6-Br | 4-$CF_3$-5,6-$F_2$-2-pyrimidyl | O | |
| 4.113 | $CH_3$ | 6-Cl | 5-Br-3-pyridazinyl | O | |
| 4.114 | $CH_3$ | 6-Cl | 4-$(CH_3)$-6-$(OCH_3)$-2-pyrimidyl | S | |
| 4.115 | $N(CH_3)_2$ | 5-Cl | 4,6-$F_2$-2-pyrimidyl | O | |
| 4.116 | $CH_3$ | 6-Br | 4-$(CF_3)$-5-COOMe-2-pyrimidyl | O | |
| 4.117 | $CH_3$ | 5-$N(CH_3)_2$ | 4-$N(Bu)_2$-5-F-2-pyrimidyl | O | |
| 4.118 | $CH_3$ | 5-H | 4-$OC_4H_9$-2-pyrimidyl | O | |
| 4.119 | $CH_3$ | 5-Cl | 4-(Cl)-5-$(CH_3)$-2-pyrimidyl | S | |
| 4.120 | $CH_3$ | 5-H | 4,6-$(OMe)_2$-2-pyrimidyl | O | |
| 4.121 | $CH_3$ | 5-H | 2,6-$Cl_2$-1-pyrimidyl | S | |
| 4.122 | Bu | 6-F | 2-Cl,6-$CH_3$-4-pyrimidyl | S | |
| 4.123 | $CH_3$ | 6-Br | 2-Cl-5-$CH_3$-4-pyrimidyl | S | |
| 4.124 | $CH_3$ | 5-Cl | 5-Cl-6-Et-4-pyrimidyl | O | |
| 4.125 | $CH_3$ | 5-H | 2,6-$(MeO)_2$-4-pyrimidyl | S | |
| 4.126 | i-Pr | 6-Cl | 2-Cl,5-F-4-pyrimidyl | O | |
| 4.127 | $CH_3$ | 5-$OCF_3$ | 2,5-$F_2$-6-$CF_3$-4-pyrimidyl | O | |
| 4.128 | $CH_3$ | 5-i-$C_3H_7$ | 2-Cl-6-$N(CH_3)_2$-4-pyrimidyl | S | |
| 4.129 | $CH_3$ | 6-Br | 2,6-$F_2$-4-pyrimidyl | O | |
| 4.130 | $CH_3$ | 5-Cl | 2-SMe-6-Me-4-pyrimidyl | S | |
| 4.131 | $CH_3$ | 5-H | 2-S-Pr-4-pyrimidyl | O | |
| 4.132 | $CH_3$ | 6-Cl | 2-Cl-4-pyrimidyl | O | |
| 4.133 | $CH_3$ | 5-$OCH_3$ | 2-SMe-6-Cl-4-pyrimidyl | S | |
| 4.134 | Bu | 5-On-$C_3H_7$ | 6-SMe-4-pyrimidyl | O | |
| 4.135 | $CH_3$ | 5-H | 2-$CH_2$-5-pyrimidyl | S | |
| 4.136 | $CH_3$ | 6-Cl | 4-Cl-5-pyrimidyl | O | |
| 4.137 | $CH_3$ | 5-$CH_3$ | 2-SBu-5-pyrimidyl | O | |
| 4.138 | $CH_3$ | 6-Br | 2-CN-4-$NO_2$-5-pyrimidyl | S | |
| 4.139 | $CH_3$ | 6-$N(CH_3)_2$ | 2-MeO-5-pyrimidyl | O | |
| 4.140 | $N(CH_3)_2$ | 5-H | 2-COOMe-5-pyrimidyl | S | |
| 4.141 | $CH_3$ | 6-Cl | 4-$N(Bu)_2$-5-pyrimidyl | O | |
| 4.142 | $CH_3$ | 6-Cl | 2,4-$Cl_2$-5-pyrimidyl | O | |
| 4.143 | $CH_3$ | 6-$CF_3$ | 2,4-$(CH_3)_2$-5-pyrimidyl | S | |
| 4.144 | Bu | 5-H | 2-pyrazinyl | O | |
| 4.145 | $CH_3$ | 5-Cl | 3-chloro-2-pyrazinyl | S | |
| 4.146 | $CH_3$ | 5-Br | 6-chloro-2-pyrazinyl | S | |
| 4.147 | $CH_3$ | 6-Cl | 3,6-$Me_2$-2-pyrazinyl | S | |
| 4.148 | $CH_3$ | 5-$CF_3$ | 3-pyridazinyl | O | |
| 4.149 | $CH_3$ | 6-Br | 3,5-$(NBu_2)_2$-6-CN-2-pyrazinyl | S | |
| 4.150 | $CH_3$ | 6-Cl | 3,5,6-$(CH_3)_3$-2-pyrazinyl | O | |
| 4.151 | $CH_3$ | 5-Br | 3-Et-2-pyrazinyl | O | |
| 4.152 | $CH_3$ | 6-Cl | 5-OMe-2-pyrazinyl | O | |
| 4.153 | $CH_3$ | 6-Br | 6-Br-2-pyrazinyl | O | |
| 4.154 | $CH_3$ | 5-H | 5-OMe-2-pyrazinyl | O | |
| 4.155 | $N(CH_3)_2$ | 5-Cl | 3-$NO_2$-2-pyrazinyl | O | |
| 4.156 | $CH_3$ | 5-Br | 3,5$(Cl)_2$-2-pyridyl | S | |
| 4.157 | $CH_3$ | 6-Cl | 3,5$(Cl)_2$-2-pyridyl | O | |
| 4.158 | $CH_3$ | 6-Cl | 3-Cl,5F-2-pyridyl | O | |
| 4.159 | $N(CH_3)_2$ | 6-Br | 3-Cl,5F-2-pyridyl | S | |
| 4.160 | $CH_3$ | 5-F | 3-Cl,5$(CF_3)$-2-pyridyl | O | |
| 4.161 | $CH_3$ | 6-Cl | 3-Cl,5$(CF_3)$-2-pyridyl | S | |
| 4.162 | $CH_3$ | 5-Br | 3-Cl,5$(CF_3)$-2-pyridyl | S | |
| 4.163 | $CH_3$ | 6-Cl | 4,6$(OCH_3)_2$-2-pyrimidyl | S | |
| 4.164 | $CH_3$ | 6-Br | 4,6$(OCH_3)_2$-2-pyrimidyl | O | |

Bu = n-$C_4H_9$

Formulation Examples for active ingredients of formula I (throughout, percentages are by weight)

| 2.1. Wettable powders | a) | b) | c) |
|---|---|---|---|
| a compound of the Tables | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 mol of ethylene oxide) | — | 2% | — |
| highly dispersed silicic acid | 5% | 10% | 10% |

-continued

| 2.1. Wettable powders | a) | b) | c) |
|---|---|---|---|
| kaolin | — | 62% | 27% |

The active ingredient is thoroughly mixed with the adjuvants and the mixture is thoroughly ground in a suitable mill, affording wettable powders which can be diluted with water to give suspensions of the desired concentration.

| 2.2. Emulsifiable concentrate | |
|---|---|
| a compound of the Tables | 10% |
| octylphenol polyethylene glycol ether (4–5 mol of ethylene oxide) | 3% |
| calcium dodecylbenzenesulfonate | 3% |
| castor oil polyglycol ether (35 mol of ethylene oxide) | 4% |
| cyclohexanone | 34% |
| xylene mixture | 50% |

Emulsions of any desired concentration can be obtained from this concentrate by dilution with water.

| 2.3. Dusts | a) | b) |
|---|---|---|
| a compound of the Tables | 5% | 8% |
| talcum | 95% | — |
| kaolin | — | 92% |

Ready-for-use dusts are obtained by mixing the active ingredient with the carrier and grinding the mixture in a suitable mill.

| 2.4. Extruder granules | |
|---|---|
| a compound of the Tables | 10% |
| sodium lignosulfonate | 2% |
| carboxymethylcellulose | 1% |
| kaolin | 87% |

The active ingredient is mixed and ground with the adjuvants, and the mixture is moistened with water. The mixture is extruded and then dried in a stream of air.

| 2.5. Coated granules | |
|---|---|
| a compound of the Tables | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granules are obtained in this manner.

| 2.6. Suspension concentrate | |
|---|---|
| a compound of the Tables | 40% |
| ethylene glycol | 10% |
| nonylphenol polyethylene glycol ether (15 mol of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

3. Biological Examples

Example 3.1: Action Against *Plasmopara viticola* on Vines a) Residual protective action Vine seedlings in the 4–5 leaf stage are sprayed with a spray mixture (0.02% active ingredient) prepared from a wettable powder formulation of the test compound. After 24 hours the treated plants are infected with a sporangia suspension of the fungus. Fungus attack is evaluated after incubation for 6 days at 95–100% relative humidity and 20° C.

b) Residual curative action

Vine seedlings in the 4–5 leaf stage are infected with a sporangia suspension of the fungus. After incubation for 24 hours in a humidity chamber at 95–100% relative humidity and 20° C., the infected plants are dried and sprayed with a spray mixture (0.02% active ingredient) prepared from a wettable powder formulation of the test compound. After the spray coating has dried, the treated plants are again placed in the humidity chamber. Evaluation of fungus attack is made 6 days after infection.

Compounds of the Tables exhibit very good fungicidal activity against *Plasmopara viticola* on vines, and in particular compounds nos. 1.20, 1.68 and 1.125 inhibit fungus attack completely (0 to 5% residual attack). On the other hand, Plasmopara attack is 100% on untreated and infected control plants.

Example 3.2: Action Against Phytophthora on Tomato Plants a) Residual protective action After a cultivation period of 3 weeks, tomato plants are sprayed with a spray mixture (0.02% active ingredient) prepared from a wettable powder formulation of the test compound. After 24 hours the treated plants are infected with a sporangia suspension of the fungus. The infected plants are then incubated for 5 days at 90–100% relative humidity and 20° C. and then evaluated for fungus attack.

b) Systemic action

After a cultivation period of 3 weeks, a spray mixture (0.002% active ingredient, based on the volume of soil) prepared from a wettable powder formulation of the test compound is used to water tomato plants. Care is taken that the spray mixture does not come into contact with the parts of the plants above the soil. The treated plants are infected 48 hours later with a sporangia suspension of the fungus. The infected plants are then incubated for 5 days at 90–100% relative humidity and 20° C. and then evaluated for fungus attack Compounds of the Tables exhibit a lasting effect (less than 20% fungus attack). Compounds Nos. 1.20, 1.68 and 1.156 inhibit fungus attack almost completely (0 to 5% attack). On the other hand, Phytophthora attack is 100% on untreated and infected control plants.

Example 3.3: Action Against Phytophthora on Potato Plants a) Residual protective action After a cultivation period of 3 weeks, 2- to 3-week old potato plants (Bintje variety) are sprayed with a spray mixture (0.02% active ingredient) prepared from a wettable powder formulation of the test compound. The treated plants are infected 24 hours later with a sporangia suspension of the fungus. The infected plants are then incubated for 5 days at 90–100% relative humidity and 20° C. and then evaluated for fungus attack.

b) Systemic action

After a cultivation period of 3 weeks, a spray mixture (0.002% active ingredient, based on the volume of soil) prepared from a wettable powder formulation of the test compound, is used to water 2- to 3-week old potato plants (Bintje variety). Care is taken that the spray mixture does not come into contact with the parts of the plants above the soil. The treated plants are infected 48 hours later with a sporangia suspension of the fungus. The infected plants are then incubated for 5 days at 90–100% relative humidity and 20° C. and then evaluated for fungus attack.

Compounds of the Tables exhibit a lasting effect (less than 20% fungus attack). Compounds nos. 1.20, 1.68 and 1.156 inhibit fungus attack almost completely (0 to 5% attack). On the other hand, Phytophthora attack is 100% on untreated and infected control plants.

What is claimed is:

1. A benzotriazolesulfonic acid derivative of formula I

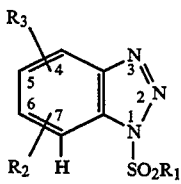

wherein the $R_1SO_2$ group occupies the 1- or the 3-position and, in relation to the substituents $R_3$ and $R_2$, forms pure isomers or a mixture of structural isomers, and wherein the substituents are defined as follows:

$R_3 = R_4X$ $X$ = oxygen or sulfur;

$R_4$ = unsubstituted pyridine or pyridine which is substituted by one to three substituents selected from halogen, $C_1$–$C_6$alkyl, $C_1$–$C_6$alkoxy, $C_1$–$C_6$alkylthio, $C_1$–$C_6$haloalkyl, $C_1$–$C_6$haloalkoxy, $C_3$–$C_6$cycloalkyl, cyano, nitro, —COO($C_1$–$C_6$alkyl) and $N(R')(R'')$;

$R_2$ = hydrogen, halogen, $C_1$–$C_4$alkyl, $C_1$–$C_4$alkoxy, $C_1$–$C_4$haloalkyl, $C_1$–$C_4$haloalkoxy or -N(alk)$_2$;

$R_1$ = $C_1C_4$alkyl, $C_1$–$C_4$haloalkyl, $C_3$–$C_6$cycloalkyl, or -N(alk)$_2$, wherein each alk is $C_1$–$C_4$alkyl and, whether the same or different, is bonded to N;

$R'$ and $R''$ = independently, hydrogen or $C_1$–$C_4$alkyl.

2. A benzotriazolesulfonic acid derivative of formula I, according to claim 1, wherein the $R_1SO_2$ group occupies the 1- or the 3-position and, in relation to the substituents $R_3$ and $R_2$, forms pure isomers or a mixture of structural isomers, and wherein the substituents are defined as follows:

$R_3 = R_4X$ $X$ = oxygen or sulfur;

$R_4$ = unsubstituted pyridine or pyridine which is substituted by one to three substituents selected from halogen, $C_1$–$C_6$alkyl, $C_1$–$C_6$alkoxy, $C_1$–$C_6$alkylthio, $C_1$–$C_6$haloalkyl, $C_1$–$C_6$haloalkoxy, cyano, nitro, —COO($C_1$–$C_6$alkyl) and $N(R')(R'')$;

$R_2$ = hydrogen, halogen, $C_1$–$C_4$alkyl, $C_1$–$C_4$alkoxy, $C_1$–$C_4$haloalkyl, $C_1$–$C_4$haloalkoxy or -N(alk)$_2$;

$R_1$ = $C_1$–$C_4$alkyl, $C_1$–$C_4$haloalkyl, $C_3$–$C_6$cycloalkyl, or -N(alk)$_2$, wherein each alk is $C_1$–$C_4$alkyl and, whether the same or different, is bonded to N;

$R'$ and $R''$ = independently, hydrogen or $C_1$–$C_4$alkyl.

3. A compound according to claim 2 wherein $R_4$ is a substituted pyridine.

4. A compound according to claim 1 wherein $R_4$ is pyridine, and is substituted by from one to three substituents selected from halogen, methyl, ethyl, isopropyl, methoxy, $C_1$–$C_2$haloalkyl wherein the halogen is F and/or Cl, $CF_3O$, $CHF_2O$, cyclopropyl and nitro.

5. A compound according to claim 3 wherein substituted pyridine is substituted by from one to three substituents selected from halogen, methyl, ethyl, isopropyl, methoxy, $C_1$–$C_2$haloalkyl wherein the halogen is F and/or Cl, $CF_3O$, $CHF_2O$ and nitro.

6. A compound according to claim 2 wherein $R_2$ is hydrogen, fluorine, chlorine, bromine, methyl, methoxy, $CF_3$, $CF_3O$ or $CHF_2O$.

7. A compound according to claim 6 wherein $R_2$ is hydrogen, chlorine or bromine.

8. A compound according to claim 1 wherein $R_4$ is pyridine and the pyridine ring is substituted by a maximum of three substituents selected from halogen, $C_1$–$C_4$alkyl, $C_1$–$C_4$alkoxy, $C_1$–$C_4$haloalkyl, $C_1$–$C_4$haloalkoxy and cyclopropyl.

9. A compound according to claim 6 wherein the pyridine ring is substituted by a maximum of three substituents selected from halogen, $C_1$–$C_4$alkyl, $C_1$–$C_4$alkoxy, $C_1$–$C_4$haloalkyl and $C_1$–$C_4$haloalkoxy.

10. A compound according to claim 9 wherein the pyridine ring is substituted by $CF_3$.

11. A compound according to claim 2 wherein $R_1$ is methyl.

12. A compound according to claim 2 wherein the 4-position of the benzotriazole ring is unsubstituted.

13. A composition for controlling and preventing an attack on plants by microorganisms, which comprises as active ingredient a microbicidally effective amount of a compound of formula I according to claim 1 together with a suitable carrier.

14. A method of controlling and preventing an attack on plants by microorganisms, which comprises applying a microbicidally effective amount of a compound of formula I according to claim 1 to the plants, to parts of the plants or to the nutrient soil of the plants.

15. A composition for controlling or preventing an attack on plants by microorganisms, which comprises a microbicidally effective amount of a compound of claim 2 and a carrier.

16. A method of controlling and preventing an attack on plants by microorganisms, which comprises applying a microbicidally effective amount of a compound of claim 2 to the plants, parts of the plants or the nutrient soil of the plants.

* * * * *